US012782349B2

(12) United States Patent
Morishita et al.

(10) Patent No.: US 12,782,349 B2
(45) Date of Patent: Nov. 3, 2026

(54) METHOD FOR EVALUATING INTERACTION BETWEEN IMMOBILIZED SUBSTANCE IMMOBILIZED DIRECTLY OR INDIRECTLY ON SUBSTRATE AND PROXIMITY-DEPENDENT MODIFYING ENZYME-LABELED SUBSTANCE TO BE ANALYZED

(71) Applicant: CELLFREE SCIENCES CO., LTD., Ehime (JP)

(72) Inventors: Ryo Morishita, Kanagawa (JP); Shusei Sugiyama, Kanagawa (JP); Miwako Denda, Kanagawa (JP)

(73) Assignee: CELLFREE SCIENCES CO., LTD., Ehime (JP)

( * ) Notice: Subject to any disclaimer, the term of this patent is extended or adjusted under 35 U.S.C. 154(b) by 891 days.

(21) Appl. No.: 18/015,086

(22) PCT Filed: Jul. 9, 2021

(86) PCT No.: PCT/JP2021/026051
§ 371 (c)(1),
(2) Date: Jan. 9, 2023

(87) PCT Pub. No.: WO2022/009994
PCT Pub. Date: Jan. 13, 2022

(65) Prior Publication Data

US 2023/0251254 A1 Aug. 10, 2023

(30) Foreign Application Priority Data

Jul. 10, 2020 (JP) ................................. 2020-119556

(51) Int. Cl.
*G01N 33/543* (2006.01)

(52) U.S. Cl.
CPC . *G01N 33/54386* (2013.01); *G01N 33/54326* (2013.01)

(58) Field of Classification Search
None
See application file for complete search history.

(56) References Cited

U.S. PATENT DOCUMENTS

2016/0002701 A1* 1/2016 Farrell ................ G01N 33/581 435/7.5

FOREIGN PATENT DOCUMENTS

JP 2005069988 A 3/2005
JP 2016512324 A 4/2016

OTHER PUBLICATIONS

Fernandez-Suarez et al., "Protein-Protein Interaction Detection in Vitro and in Cells by Proximity Biotinylation", J. Am. Chem. Soc. 2008, 130, 9251-9253.*
Remnant et al., "In vitro BioID: mapping the CENP-A microenvironment with high temporal and spatial resolution", Molecular Biology of the Cell, 2019, vol. 30, p. 1314-1325.*
Kulyyassov et al. "PUB-MS: A Mass Spectrometry-based Method to Monitor Protein-Protein Proximity in vivo", Journal of Proteome Research, Aug. 15, 2011, vol. 10, pp. 4416-4427.*
Kido et al., "AirID, a novel proximity biotinylation enzyme, for analysis of protein-protein interactions", eLife, May 11, 2020, vol. 9, e54982 (24 pages).*
International Search Report and Written Opinion (with English translation of International Search Report) issued in corresponding International Patent Application No. PCT/JP2021/026051 mailed Sep. 21, 2021 (12 pages).
Kido et al., "AirID, a novel proximity biotinylation enzyme, for analysis of protein-protein interactions," eLife, May 11, 2020, vol. 9, e54983 (24 pages).
Remnant et al., "In vitro BioID: mapping the CENP-A microenvironment with high temporal and spatial resolution," Molecular Biology of the Cell, May 15, 2019, vol. 30, pp. 1314-1325.
Fernandez-Suarez et al., "Protein-Protein Interaction Detection in Vitro and in Cells by Proximity Biotinylation," Journal of the American Chemical Society, Jun. 2008, vol. 130, pp. 9251-9253.

* cited by examiner

*Primary Examiner* — Ann Montgomery
(74) *Attorney, Agent, or Firm* — Kilyk & Bowersox, P.L.L.C.

(57) ABSTRACT

A related-art interaction analysis method has been insufficient for detecting weak interactions. The inventors of the present invention have recognized that a method of evaluating an interaction between an immobilized substance immobilized directly or indirectly on a substrate and a substance to be analyzed that is labeled with a proximity-dependent modifying enzyme can solve the above-mentioned problem. Thus, the present invention has been completed.

9 Claims, 10 Drawing Sheets

Specification includes a Sequence Listing.

| SEQUENCE | LABELING TEMPERATURE | SUBSTANCE TO BE ANALYZED | IMMOBILIZED SUBSTANCE, SIGNAL VALUES SHOWN IN PARENTHESES | | | | | |
|---|---|---|---|---|---|---|---|---|
| | | | RelA | MDM2 | RelA | MDM2 | RelA | MDM2 |
| LABELING TIME | | | 30 min (OTHER THAN BioID) 6h (BioID) | | 1h (OTHER THAN BioID) 12h (BioID) | | 3h (OTHER THAN BioID) 24h (BioID) | |
| BioID SEQ ID NO:1 | 26°C | Iκβα | N/A | N/A | N/A | N/A | N/A | N/A |
| | | TP53 | N/A | N/A | N/A | N/A | N/A | N/A |
| BioID SEQ ID NO:1 | 37°C | Iκβα | N/A | N/A | N/A | N/A | 12460) | (4530) |
| | | TP53 | N/A | N/A | N/A | N/A | (1860) | (13720) |
| TurboID SEQ ID NO:2 | 26°C | Iκβα | (>DUP) | (7030) | >DUP) | >DUP) | (>DUP) | >DUP) |
| | | TP53 | (10200) | (>DUP) | DUP) | >DUP) | >DUP) | (>DUP) |
| AirID SEQ ID NO:3 | 26°C | Iκβα | (7940) | (370) | (28050) | (690) | (48000) | (520) |
| | | TP53 | (450) | (8800) | 2320) | >DUP) | (390) | (>DUP) |
| AirID-S118G MUTANT SEQ ID NO:12 | 26°C | Iκβα | (9570) | (240) | 10150) | (220) | 51370) | (370) |
| | | TP53 | 90) | (8350) | (310) | 10010) | (240) | (49900) |
| AVVA-R118S MUTANT SEQ ID NO:13 | 26°C | Iκβα | 3020) | (320) | (11130) | (310) | 50010) | (330) |
| | | TP53 | (160) | (7440) | (120) | 13300) | (180) | (24500) |
| AVVA-R118G MUTANT SEQ ID NO:14 | 26°C | Iκβα | (6900) | (140) | 7400) | (230) | (39440) | (310) |
| | | TP53 | (110) | (8300) | (210) | 13670) | (200) | 51300) |
| AVVA-R118S,Q141R MUTANT SEQ ID NO:15 | 26°C | Iκβα | (10380) | (120) | 37530) | (190) | (>DUP) | (230) |
| | | TP53 | (200) | (10440) | (130) | 23380) | (170) | >DUP) |
| AVVA-R118G,Q141R MUTANT SEQ ID NO:16 | 26°C | Iκβα | 2630) | (550) | 10080) | (280) | (>DUP) | (430) |
| | | TP53 | (180) | (9200) | (400) | 7700) | (480) | (59300) |

N/A: NO SIGNAL

>DUP: SIGNAL VALUE LARGER THAN DETECTION UPPER LIMIT VALUE (65,000)

FIG. 8

| | LABELING CONDITIONS (TEMPERATURE AND TIME) | SIGNAL VALUES (UNITLESS) RELATIVE TO NEGATIVE CONTROL FOR VARYING LAS4000 EXPOSURE TIMES | | | |
|---|---|---|---|---|---|
| | | 10sec | 1 min | 5 min | 15 min |
| BioID SEQ ID NO:1 | 37°C 24 h | 213 | 152 | 989 | 2600 |
| TurboID SEQ ID NO:2 | 26°C 30 min | 690 | 6050 | 17080 | 34890 |
| AirID SEQ ID NO:3 | 26°C 3 h | 0 | 123 | 142 | 624 |
| AirID-S118G MUTANT SEQ ID NO:12 | 26°C 3 h | 0 | 476 | 410 | 448 |
| AVVA-R118S MUTANT SEQ ID NO:13 | 26°C 3 h | 0 | 0 | 16 | 23 |
| AVVA-R118G MUTANT SEQ ID NO:14 | 26°C 3 h | 0 | 0 | 117 | 200 |
| AVVA-R118S,Q141R MUTANT SEQ ID NO:15 | 26°C 3 h | 0 | 88 | 110 | 138 |
| AVVA-R118G,Q141R MUTANT SEQ ID NO:16 | 26°C 3 h | 0 | 96 | 120 | 413 |

FIG. 9

METHOD FOR EVALUATING INTERACTION BETWEEN IMMOBILIZED SUBSTANCE IMMOBILIZED DIRECTLY OR INDIRECTLY ON SUBSTRATE AND PROXIMITY-DEPENDENT MODIFYING ENZYME-LABELED SUBSTANCE TO BE ANALYZED

TECHNICAL FIELD

The present application is a National Stage Application of PCT/JP2021/026051, filed Jul. 9, 2021, which claims priority from Japanese Patent Application No. 2020-119556, which is incorporated herein by reference. The present invention relates to a method of evaluating an interaction between an immobilized substance immobilized directly or indirectly on a substrate and a substance to be analyzed that is labeled with a proximity-dependent modifying enzyme.

BACKGROUND ART

In, for example, the fields of disease research and drug discovery, analysis of interactions between biochemical substances and chemical substances is widely used as an extremely important approach to drug discovery research. In particular, "protein-protein interaction" is a generic term for interactions that occur between proteins in living bodies. It is well known that, through control by structural changes or reactions of proteins induced by such interactions, the interactions are involved in regulation of mechanisms underlying the basis of life, such as signaling, transportation, and metabolism. Such interactions have a feature such as having extremely diverse modes and being extremely varied in terms of, for example, softness and size of an acting surface, length of contact lifetime, and presence or absence of a structural change depending on protein species.

Hitherto, there has been employed a drug discovery approach involving using an enzyme as a main target protein and using a low-molecular-weight compound as a control substance. Such small molecule-protein interaction targets a hard cavity of from about 300 square angstroms to about 1,000 square angstroms that is shielded from ambient water molecules to some extent.

Meanwhile, in drug discovery targeting a protein-protein interaction, a contact surface as large as from 1,500 square angstroms to 3,000 square angstroms where ambient water molecules are involved is targeted, and as an alternative modality to a small molecule, there have been proposed various modalities, such as a medium-molecular-weight compound, a cyclic peptide, a nucleic acid, an antibody, a protein, and a cell. However, as a method of evaluating such dynamic and relatively weak interaction, a method to be performed comprehensively, at high throughput, simply, and at low cost has a high technical hurdle, and has not been put into practical use.

For example, interaction analyses involving using living cells typified by a two-hybrid method and an immunoprecipitation method, which are most generally performed, have an advantage in that an interaction with a substance retaining activity can be detected under physiological conditions. Meanwhile, there are drawbacks such as follows: kinds and amounts of nucleic acids and proteins vary depending on cell species and the cell cycle, causing a lack of comprehensiveness, and besides, a technique for detecting their interactions is limited. In addition, in order to identify an immobilized substance whose interaction has been detected, even more labor and time are required.

As a typical example of interaction analysis that does not use living cells, there is known a surface plasmon resonance (SPR) method. The method involves detecting a change in mass due to an interaction on a sensor chip as a change in angle of disappearance of reflected light caused by surface plasmon resonance, and is capable of highly accurate measurement. However, the method is not a method of performing evaluation comprehensively and at high throughput, and is unsuited for an interaction with a small change in mass, and hence its use is limited.

There is known a biochip technology or bioarray technology that does not have the above-mentioned drawbacks. In particular, when a protein is arranged on an array or a chip, the technology is called a protein chip technology or a protein array technology. This technology involves arranging and immobilizing proteins on a substrate, to thereby enable massive concurrent analysis of interactions between the proteins and a substance to be analyzed. In addition, there are advantages in terms of simplicity of operation and cost. Cost per data point can be reduced to from about 1/10 to about 1/100. Numerous protein array technologies have been proposed, used as important tools for understanding of life phenomena or drug discovery and development, and widely used for analysis of interactions, such as protein-antibody interactions (for example, Jeong J S, et al., Mol Cell Proteomics, 2012 (Non Patent Literature 1) and Diehnelt C W et al., PLoS One, 2010 (Non Patent Literature 2)), protein-protein interactions (for example, Song, G. et al., Mol Cell Proteomics. 2019 (Non Patent Literature 3) and Al-Mulla, F., et., Cancer Res., 2011 (Non Patent Literature 4)), and nucleic acid-protein interactions (for example, Hu S et al., Cell, 2009 (Non Patent Literature 5) and Liu, L., et al., Nucleic Acids Res., 2019 (Non Patent Literature 6)).

Many of those protein arrays in general distribution are produced by immobilizing a substance such as a protein on a substrate surface having a nitrocellulose membrane or a hydrogel membrane formed thereon, or a substrate surface of, for example, a glass slide, a metal, a plastic, or carbon. The protein on any such substrate is immobilized in a dry or semi-dry state, and hence the immobilized protein is affected by drying, oxidation, and the like over time, resulting in a significant change in structure thereof. As a result of the structural change, the protein is changed into a denatured protein that no longer has physiological activity.

There is also a report of a protein array that is contrived so as to suppress drying (Patent Literature 1). However, after being applied, a solution containing a protein needs to be covered with a protection against drying such as a cover sheet, which takes labor, and besides, effective suppression of drying is not achieved. Accordingly, the protein array is not a practical one that can be generally used.

CITATION LIST

Patent Literature

[PTL 1] JP 2005-069988 A

Non Patent Literature

[NPL 1] Jeong J S, et al., Mol Cell Proteomics, 2012 (DOI: 10.1074/mcp.O111.016253)
[NPL 2] Diehnelt C W et al., PLoS One, 2010 (Doi: 10.1371/journal.pone.0010728)
[NPL 3] Song, G. et al., Mol cell Proteomics. 2019 (DOI: 10.1074/mcp.RA118.000851)

[NPL 4] Al-Mulla, F., et., Cancer Res., 2011 (DOI: 10.1158/0008-5472.CAN-10-3102)

[NPL 5] Hu S et al., Cell, 2009 (Doi: 10.1016/j.cell.2009.08.037.)

[NPL 6] Liu, L., et al., Nucleic Acids Res., 2019 (Doi: 10.1093/nar/gkz032)

SUMMARY OF INVENTION

Technical Problem

As host factors serving as targets for drug discovery and modalities that bind thereto become more diverse, it is becoming increasingly important to evaluate a protein-protein interaction, a peptide-protein interaction, a nucleic acid-protein interaction, a medium-molecular-weight compound-protein interaction, and a low-molecular-weight compound-protein interaction. A related-art interaction analysis method has been insufficient for detecting those interactions (in particular, weak interactions).

Solution to Problem

The inventors of the present invention have recognized that a method of evaluating an interaction between an immobilized substance immobilized directly or indirectly on a substrate and a substance to be analyzed that is labeled with a proximity-dependent modifying enzyme can solve the above-mentioned problem. Thus, the present invention has been completed. That is, the present invention is as described below.

1. A method of evaluating an interaction between an immobilized substance immobilized directly or indirectly on a substrate and a substance to be analyzed that is labeled with a proximity-dependent modifying enzyme, the method including the steps of:
   (1) adding a substance to be analyzed that is labeled with a proximity-dependent modifying enzyme to an immobilized substance immobilized directly or indirectly on a substrate in the presence of a labeling substance; and
   (2) detecting the labeling substance.

2. The evaluation method according to the above-mentioned item 1, further including a step of washing the substrate between the step (1) and the step (2).

3. The evaluation method according to the above-mentioned item 1 or 2, wherein the interaction has a binding dissociation constant of $1\times10^{-8}$ M or more.

4. The evaluation method according to any one of the above-mentioned items 1 to 3, wherein the immobilized substance is a protein in a solution.

5. The evaluation method according to any one of the above-mentioned items 1 to 4, wherein the immobilized substance is a non-denatured protein.

6. The evaluation method according to any one of the above-mentioned items 1 to 5, wherein the proximity-dependent modifying enzyme is an altered biotinylation enzyme reduced in substrate specificity, and wherein the labeling substance is biotin.

7. The evaluation method according to any one of the above-mentioned items 1 to 6, wherein the altered biotinylation enzyme is any one or more of the following polypeptides:
   (1) a polypeptide formed of an amino acid sequence set forth in SEQ ID NO: 1;
   (2) a polypeptide formed of an amino acid sequence set forth in SEQ ID NO: 2;
   (3) a polypeptide formed of an amino acid sequence set forth in SEQ ID NO: 3;
   (4) a polypeptide formed of an amino acid sequence set forth in SEQ ID NO: 12;
   (5) a polypeptide formed of an amino acid sequence set forth in SEQ ID NO: 13;
   (6) a polypeptide formed of an amino acid sequence set forth in SEQ ID NO: 14;
   (7) a polypeptide formed of an amino acid sequence set forth in SEQ ID NO: 15;
   (8) a polypeptide formed of an amino acid sequence set forth in SEQ ID NO: 16;
   (9) a polypeptide that has 1 to 10 amino acids substituted, deleted, inserted, and/or added in any one of the amino acid sequences set forth in SEQ ID NOS: 1 to 3 and 12 to 16, and that has substantially equivalent biotinylation enzyme activity to that of a polypeptide formed of any one of the amino acid sequences set forth in SEQ ID NOS: 1 to 3 and 12 to 16; and
   (10) a polypeptide that has 90% or more identity to any one of the amino acid sequences set forth in SEQ ID NOS: 1 to 3 and 12 to 16, and that has substantially equivalent biotinylation enzyme activity to that of a polypeptide formed of any one of the amino acid sequences set forth in SEQ ID NOS: 1 to 3 and 12 to 16.

8. The evaluation method according to any one of the above-mentioned items 1 to 7, further including adding a binding recruiter.

9. The evaluation method according to any one of the above-mentioned items 1 to 8, wherein the immobilized substance is a membrane protein, and wherein the substance to be analyzed is an antigen-binding substance.

10. A method of evaluating a protein serving as an immobilized substance indirectly immobilized on an array via magnetic beads and a substance to be analyzed that is labeled with an altered biotinylation enzyme reduced in substrate specificity, the method including the steps of:
   (1) adding a substance to be analyzed that is labeled with an altered biotinylation enzyme to an immobilized substance indirectly immobilized on an array via magnetic beads in the presence of biotin; and
   (2) detecting the biotin.

11. The evaluation method according to the above-mentioned item 10, further including a step of washing the array between the step (1) and the step (2).

12. The evaluation method according to the above-mentioned item 10 or 11, wherein the interaction has a binding dissociation constant of $1\times10^{-8}$ M or more.

13. The evaluation method according to any one of the above-mentioned items 10 to 12, wherein the immobilized substance is a protein in a solution.

14. The evaluation method according to any one of the above-mentioned items 10 to 12, wherein the immobilized substance is a non-denatured protein.

15. The evaluation method according to any one of the above-mentioned items 10 to 14, wherein the proximity-dependent modifying enzyme is an altered biotinylation enzyme reduced in substrate specificity, and wherein the labeling substance is biotin.

16. The evaluation method according to any one of the above-mentioned items 10 to 15, wherein the altered biotinylation enzyme is any one or more of the following polypeptides:
   (1) a polypeptide formed of an amino acid sequence set forth in SEQ ID NO: 1;

(2) a polypeptide formed of an amino acid sequence set forth in SEQ ID NO: 2;

(3) a polypeptide formed of an amino acid sequence set forth in SEQ ID NO: 3;

(4) a polypeptide formed of an amino acid sequence set forth in SEQ ID NO: 12;

(5) a polypeptide formed of an amino acid sequence set forth in SEQ ID NO: 13;

(6) a polypeptide formed of an amino acid sequence set forth in SEQ ID NO: 14;

(7) a polypeptide formed of an amino acid sequence set forth in SEQ ID NO: 15;

(8) a polypeptide formed of an amino acid sequence set forth in SEQ ID NO: 16;

(9) a polypeptide that has 1 to 10 amino acids substituted, deleted, inserted, and/or added in any one of the amino acid sequences set forth in SEQ ID NOS: 1 to 3 and 13 to 16, and that has substantially equivalent biotinylation enzyme activity to that of a polypeptide formed of any one of the amino acid sequences set forth in SEQ ID NOS: 1 to 3 and 13 to 16; and

(10) a polypeptide that has 90% or more identity to any one of the amino acid sequences set forth in SEQ ID NOS: 1 to 3 and 13 to 16, and that has substantially equivalent biotinylation enzyme activity to that of a polypeptide formed of any one of the amino acid sequences set forth in SEQ ID NOS: 1 to 3 and 13 to 16.

17. The evaluation method according to any one of the above-mentioned items 10 to 16, further including adding a binding recruiter.

18. The evaluation method according to any one of the above-mentioned items 10 to 17, wherein the immobilized substance is a membrane protein, and wherein the substance to be analyzed is an antigen-binding substance.

Advantageous Effects of Invention

Through use of the method of evaluating an interaction between an immobilized substance immobilized directly or indirectly on a substrate and a substance to be analyzed that is labeled with a proximity-dependent modifying enzyme (in particular, a protein-protein interaction) of the present invention, an interaction that has not been able to be detected by a related-art evaluation method has been able to be detected.

BRIEF DESCRIPTION OF DRAWINGS

FIG. 8 shows results of Example 4.

FIG. 9 shows results of Example 4.

DESCRIPTION OF EMBODIMENTS (The Present Invention)

Figure 1:
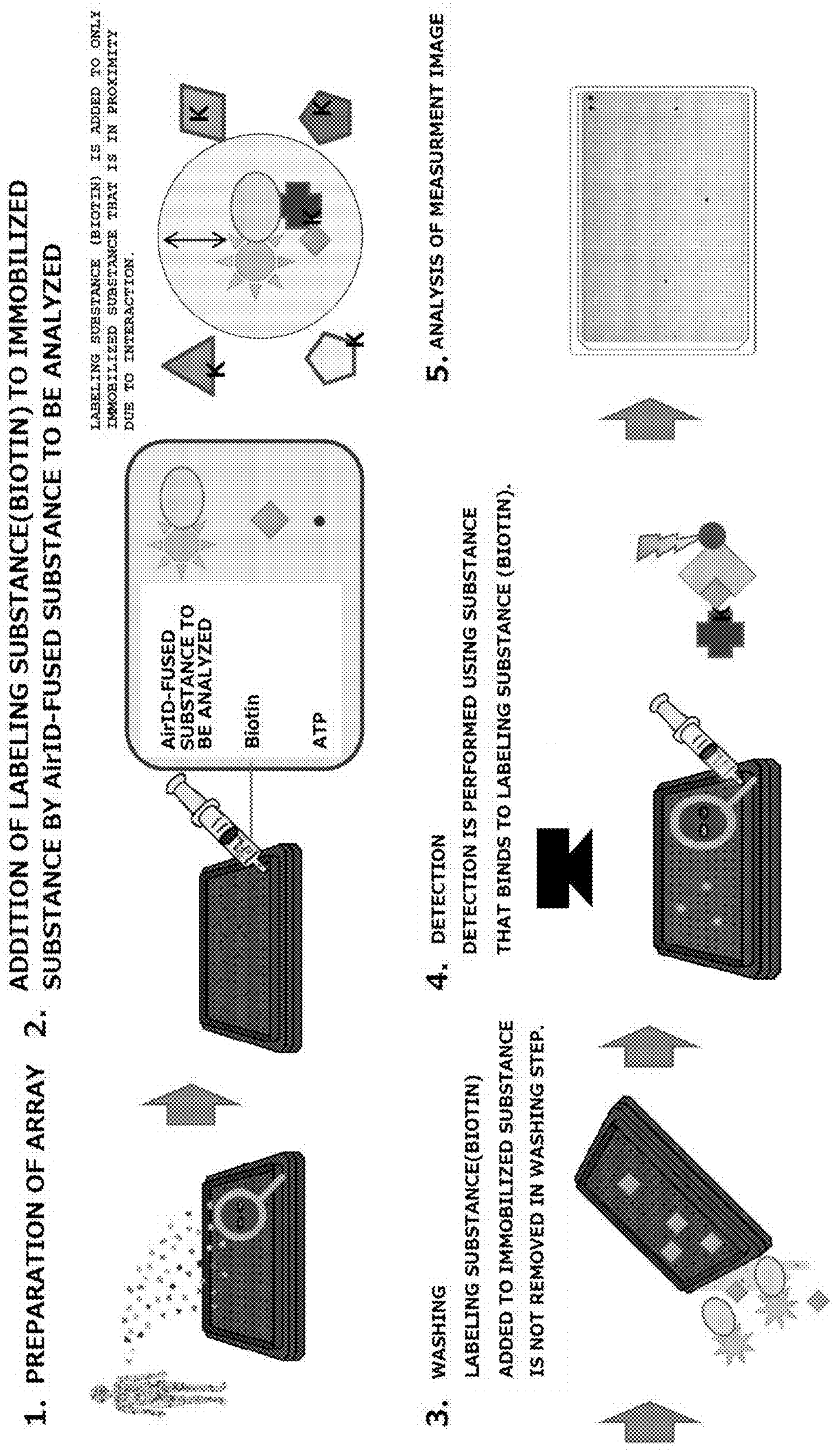
FIG. 1 is an illustration of an example of the steps of an evaluation method of the present invention.

The present invention relates to a method of evaluating an interaction between an immobilized substance immobilized directly or indirectly on a substrate and a substance to be analyzed that is labeled with a proximity-dependent modifying enzyme (hereinafter sometimes referred to as "evaluation method of the present invention"), the method including the steps of:

(1) adding a substance to be analyzed that is labeled with a proximity-dependent modifying enzyme to an immobilized substance immobilized directly or indirectly on a substrate in the presence of a labeling substance; and (2) detecting the labeling substance.

The evaluation of the interaction between the immobilized substance and the substance to be analyzed includes detecting or quantifying transient or continuous binding between the immobilized substance and the substance to be analyzed.

The method preferably includes a step of washing the substrate between the above-mentioned step (1) and the above-mentioned step (2).

(Substrate)

As the substrate, there may be used a substrate known per se for, for example, detecting binding between an immobilized substance and a substance to be analyzed. The shape of the substrate may be a flat plate shape, or may be a so-called ELISA plate shape. In addition, a flat plate serving as the substrate and having minute dimple-shaped depressions formed thereon, or a substrate having a porous membrane or a nitrocellulose membrane formed on its surface may be adopted. In addition, a pad for arraying a protein may be formed as well. As a method of performing such processing, molding processing, a lithographic technology, or the like may be appropriately selected in accordance with a material for the substrate. A low-background material is desirably used as the material for the substrate so as not to affect the detection of luminescence or fluorescence to be used for subsequent detection of the interaction. Suitable examples of the material for the substrate include non-fluorescent glass, amorphous carbon, quartz, polystyrene, polycarbonate, polymethyl methacrylate, polyolefin, polyethylene terephthalate, and a cycloolefin copolymer.

(Array)

The term "array" as used in the present invention refers to a product obtained by arranging and immobilizing immobilized substances directly or indirectly on a substrate (preferably on a substrate on which arrangement information has been specified). The array can perform the evaluation of the interactions of the substance to be analyzed with all the arranged immobilized substances at once.

(Immobilized Substance)

The immobilized substance is not particularly limited as long as the substance can be immobilized directly or indirectly on the substrate, but examples thereof may include proteins, antibodies, nucleic acids (including DNA, RNA, and the like), peptides, low-molecular-weight compounds, medium-molecular-weight compounds, cell extracts, tissue extracts, saccharides, lipids, physiologically active substances, and complexes thereof. The immobilized substance may be a single molecule or a mixture, may be a natural product, a genetically modified product, or a chemically synthesized product, and may be a derivative or a fragment. An operation, such as modification, substitution, deletion, or addition, may be performed.

(Substance to be Analyzed)

The substance to be analyzed is not particularly limited as long as the proximity-dependent modifying enzyme can directly or indirectly label the substance, but examples thereof may include proteins, antibodies, nucleic acids (including DNA, RNA, and the like), peptides, low-molecular-weight compounds, medium-molecular-weight compounds, cell extracts, tissue extracts, saccharides, lipids, physiologically active substances, and complexes thereof. As a specific example of the complex serving as the substance to be analyzed, there is given, for example, a case in which a protein A and a compound B form a complex to enable an interaction with an immobilized substance C, or to enhance the strength of the interaction. The substance to be analyzed may be a single molecule or a mixture, may be a natural product, a genetically modified product, or a chemically synthesized product, and may be a derivative or a fragment. An operation, such as modification, substitution, deletion, or addition, may be performed.

(Direct or Indirect Immobilization of Immobilized Substance on Substrate)

A known immobilization method may be adopted to immobilize the immobilized substance directly or indirectly on the substrate as long as the immobilized substance is substantially free from flowing out completely in the step of washing the substrate {Bound (B)/Free (F) separation washing step} of the evaluation method of the present invention. For example, the immobilized substance needs to be bound to the substrate by a physically or chemically appropriate method in accordance with the material for the substrate. The "indirect immobilization on the substrate" means that the immobilized substance is immobilized on the substrate via some substance (e.g., beads). The "immobilization" means being physically or chemically bound to the substrate. When the immobilized substance is a tag-fused protein having a tag fused thereto, it is appropriate to form, on the surface of the substrate, a ligand that specifically binds to the tag, an antibody that recognizes the tag, a metal chelate capable of binding to the tag, or the like. Through use of the substrate having such surface and the tag-fused protein, the immobilized substance can be immobilized directly or indirectly on the substrate by tag-ligand binding, tag-antibody binding, or tag-chelate binding. More specific examples thereof may include His tag and Ni-NTA, GST tag and glutathione, MBP tag and dextrin, biotin and avidin, biotin and streptavidin, biotin and neutravidin, FLAG™ tag and anti-FLAG™ antibody, GST tag and anti-GST antibody, and HA tag and anti-HA antibody.

When an inorganic substrate such as glass is used and a protein having no tag fused thereto is used as the immobilized substance, the surface of the substrate is preferably treated with a silane coupling agent having a functional group capable of being bonded to an amino group or a carboxyl group (e.g., an epoxy group, an active ester, an amino group, an acid anhydride group, or an isocyanate group). By spotting a solution containing the immobilized substance (in particular, a protein) on the treated substrate, the immobilized substance can be immobilized on the surface of the substrate with a covalent bond at the N-terminus or C-terminus of the protein. As the silane coupling agent, ones with various chain lengths are commercially available, any of which may be used as long as the structure of the protein is not affected. In addition, a linker may be used to adjust a binding distance between the immobilized substance (in particular, a protein) and the substrate.

As other examples, an aminooxy linker having a hydrophobic alkyl and a thiol group, a hydrazide linker, and the like may also be given as suitable examples for immobilizing a protein on a metal surface.

As a specific example, magnetic beads are used. For example, a GST-fused immobilized substance (GST-fused protein) is added to magnetic beads having a glutathione surface layer formed thereon to bind the immobilized substance to the magnetic beads via GST. The magnetic beads having the GST-fused immobilized substance (GST-fused protein) on the surface may be arranged on a substrate (in particular, an array) that has been processed into a well shape, to immobilize the GST-fused immobilized substance at a predetermined position on the substrate with a magnetic force from the back side of the substrate. In this method, which is not limited to GST, combinations of various binding modes are known to a person skilled in the art, and various choices are possible in accordance with the design of affinity required.

In addition, some tags to be fused to the immobilized substance (e.g., a protein) have an effect of improving the properties of the protein into satisfactory ones. For example, GST, FLAG™, or the like has an effect of promoting the hydration of the immobilized substance (e.g., a protein), and may be used by being fused to the immobilized substance (e.g., a protein) as appropriate. In addition, when the immobilized substance is a membrane protein, the protein may be bound, in the form of being fused to a liposome or fused to a nanodisc, to the substrate through use of the above-mentioned binding system. In addition, when the immobilized substance is a protein, for the purpose of more accurately evaluating the interaction, the protein may be brought into contact with a required enzyme in advance to be subjected to post-translational modification, such as phosphorylation, dephosphorylation, glycosylation, ubiquitination, nitrosylation, methylation, acetylation, or lipidation, or an isomerase, a flavin enzyme, a microsome, or the like may be added in order to prepare a precursor or a mature form depending on the presence or absence of processing, to form a complex through coexpression or the like, or to form a disulfide bond.

In addition, for the step of arraying the protein serving as the immobilized substance on the substrate, there may be used such a general-purpose apparatus that a required volumetric portion of a solution prepared from a trace amount of the protein can be precisely dispensed/applied at a designated position with a large dispenser, an inkjet-type spotter, or a spotter of a pin spot type or the like.

(Protein as Immobilized Substance)

It is known that a protein serving as an immobilized substance immobilized on a substrate or immobilized or arrayed on an array is denatured by being significantly affected by physical and chemical, macro- and micro-environments. In particular, at a liquid/solid interface or a liquid/gas interface, such denaturation easily proceeds irreversibly, and as a result, the protein is liable to be brought into an inactive state in which a function to be originally exhibited is lost. In a related-art method, it has been difficult owing to the inactive state to evaluate an interaction between the protein serving as the immobilized substance and the protein serving as the substance to be analyzed. That is, the protein serving as the immobilized substance is preferably kept in a non-denatured state.

It is also known that only part of the protein serving as the immobilized substance immobilized at each designated position on the array needs to retain an ability to interact with the substance to be analyzed. This is because, though depending on the kind of the protein arrayed, a substantially non-denatured protein array can be obtained as long as some part of the function remains, as described in the above-mentioned literatures relating to the analysis of interactions, such as protein-protein interactions (for example, Song, G. et al., Mol Cell Proteomics. 2019, Al-Mulla, F., et al., Cancer Res., 2011) and nucleic acid-protein interactions (for example, Hu S et al., Cell, 2009, Liu, L., et al., Nucleic Res., 2019). That is, a molecular species such as a kinase can be evaluated for its intermolecular interaction as long as the substrate protein of the kinase keeps its structure to some degree, even if the protein as a whole does not have its original structure. Accordingly, the "non-denatured state" of the protein serving as the immobilized substance means that at least a portion thereof that interacts with the substance to be analyzed maintains its shape or function.

The inventors of the present invention have succeeded in putting a non-denatured protein array into practical use for the first time in the world in order to enable the evaluation of a protein-protein interaction that is difficult to evaluate (Morishita, R., et al., Sci Rep: doi.org/10.1038/s41598-019-55785-5). This non-denatured protein array has a feature in that the protein is present in a solution in all the work/steps from the synthesis of the protein to its immobilization (arraying) on a substrate, to the storage of the substrate or array having the protein immobilized thereon, and to interaction evaluation, and hence the protein serving as the immobilized substance is not dried or oxidized and keeps its non-denatured state. However, the solution may be temporarily brought into a frozen state at the time of the storage of the protein array as long as a function related to the interaction analysis of the protein is not impaired.

More specifically, the protein serving as the immobilized substance is present in an appropriate solution such as a buffer so as not to undergo a dry state in all the steps of the synthesis, purification, arraying, and interaction evaluation of the protein. For example, the following series of steps as exemplified in Examples is one of the desired modes of the evaluation method of the present invention: a protein fused to a tag is bound to magnetic beads having such surface composition as to bind to the tag, the resultant protein-bead complex is accommodated in a well formed on an array without being brought into contact with air, and the protein-protein interaction is evaluated in a solution.

As another mode, the top of the substrate is coated in advance with an intermediate substance that binds to the protein serving as the immobilized substance. Then, a buffer solution containing the protein may be added onto the coated substrate, followed by the evaluation of the interaction before the solution is dried. It is known that, when the spot size (volume) of the protein solution becomes about 10 nanoliters as compared to the case of 1 microliter, the surface area relative to the volume is increased by about 460%, though a contribution is made to the densification of the array. As a result, inactivation of the protein is increased, and hence measures for preventing drying are all the more required. In the case of such flat-plate array, for the purpose of preventing the drying of the protein solution on the array, when the array is kept in a state of having a humidity close to 100%, the drying of the protein solution can be minimized to allow a non-denatured state to be kept for a certain period of time. For example, such humid state may be achieved through use of a saturated water vapor pressure humidification generator making use of a bubbling method or a Nafion method. Further, the protein may be kept in a non-denatured state by covering the protein solution spots formed on the array from above with a mineral oil such as liquid paraffin having low solubility to prevent evaporation. In this case, a non-denatured protein array can be achieved by gently replacing the mineral oil with an appropriate buffer immediately before allowing the substance to be analyzed to act on the protein serving as the immobilized substance on the substrate (array).

Further, as another mode, the following may also be given as a suitable example: a sugar-based surfactant is added to the solution containing the protein serving as the immobilized substance to be spotted on the array to enhance the drying resistance of the protein. As such sugar-based surfactant, ones with various alkyl chain lengths are available, but suitable examples thereof may include sucrose, trehalose, and maltose. For example, about 0.5% to about 10%, preferably 1% to 5% of the sugar-based surfactant may be added to the solution containing the protein.

(Synthesis Method for Proteins serving as Substance to be analyzed and Immobilized Substance)

A method known per se may be used as a synthesis method for proteins serving as the substance to be analyzed and the immobilized substance, but generally used recombinant proteins are desirably used because of simplicity. For example, there may be used: *Escherichia coli, Bacillus subtilis*, Sf9 insect cells, CHO cells, human cells, yeast, *Brevibacillus*, a filamentous fungus (*Aspergillus*), or tobacco BY-2 cells; *Nicotiana benthamiana*, lettuce, tomato (fruits and leaves), rice, barley, *Phalaenopsis aphrodite*, or *Capsicum annuum* using a transient expression system of a plant; or a cell-free protein synthesis system. For example, suitable examples of the cell-free protein synthesis system may include *Escherichia coli*, a reconstructed *Escherichia coli* system, wheat, an insect, yeast, tobacco, rabbit reticulocytes, and human cells. A wheat cell-free system is particularly excellent for the purpose of comprehensively obtaining a wide variety of proteins, also has an extremely high probability of allowing a protein to be synthesized in a solubilized state, and is very advantageous in terms of cost as well.

According to Professor Steven Salzberg of Johns Hopkins University, the number of human genes is 21,306 in the latest results. The use of the wheat cell-free system enables nearly genome-wide synthesis. All those genes may be arranged on an array as immobilized substances, but it is preferred that only a specific category by function or by organ be arranged.

Suitable examples of the category array include category arrays of Protein kinase, DNA binding protein, GPCR, Chaperone, Channel, PPase, E3 ligase, Epigenetics, Transporter, TM1 (single-pass transmembrane), RNA binding, Protease, CD marker, Cancer Testis Antigen, and cancer-specific protein group by organ.

In addition, when proteins that interact relatively frequently are selected from an interaction database, such as BioGRID or MINT, and a group of proteins found to frequently interact is selected and arranged on an array, a comprehensive investigation can be made on what lineages of proteins those proteins are likely to interact with.

In the case of using the wheat cell-free system, cell-free protein synthesis using the WEPRO7240 series (CellFree Sciences Co., Ltd.) uses a reagent from which a GST-like protein has been removed in advance, and hence can provide a protein having an extremely high purity through simple purification with glutathione beads. This is one of the most preferred methods of preparing many kinds of purified GST tag-fused proteins.

The immobilized substance may be a single protein including a fusion type, or may be a protein in which a plurality of kinds of proteins are mixed and complexed.

In addition, antibodies, single-chain antibodies, and nanobodies can be expected to have relatively high affinity, but some have weak affinity with a dissociation constant of $1\times10^{-8}$ M or more and serve as one form of the preferred analysis objects of the present invention. A labeling amino acid may be introduced into the protein. The protein may be synthesized under coexistence with a stable isotope amino acid, a radioisotope amino acid, or an amino acid other than the 20 standard kinds, such as selenomethionine, or tRNA having a labeling amino acid bound thereto may be added during the synthesis.

The protein may be modified, and, for example, phosphorylation, methylation, acetylation, myristoylation, or biotinylation may be performed under coexistence with a corresponding substrate or modifying enzyme. In addition, the modification may be performed using a reagent for click chemistry or the like, and may be performed during the synthesis or after the synthesis.

Complexation may be homomultimerization, or may be a heteromultimerization, and multimerization may be performed using a crosslinking agent or the like.

A complex prepared in advance in which dissimilar molecules interact with each other, such as a protein-cofactor complex, a protein-nucleic acid complex, a protein-lipid complex, or a protein-compound complex, may be used during protein synthesis or after the synthesis. Through use thereof during the synthesis, the complex can also be formed while maintaining an appropriate structure.

In particular, when a protein complex is prepared by wheat cell-free synthesis, there may be adopted a method (simultaneous batch synthesis) involving performing synthesis in which a plurality of kinds of expression templates (mRNAs) are simultaneously brought into contact with/added to a wheat cell-free extract solution (WEPRO7240 series). In addition, when the respective expression templates are each separately brought into contact with/added to the wheat cell-free extract solution, and subjected to a reaction for from about 5 minutes to about 8 hours, or preincubated for desirably from about 15 minutes to about 2 hours, more desirably from about 30 minutes to about 1 hour, at a reaction temperature (which may be appropriately selected within the range of from about 4° C. to about 37° C.), and then the solutions are mixed to cause translation reactions to proceed, stoichiometric self-complexation is easily promoted. For the mixing, the order of reactions may be appropriately designed in consideration of, for example, a desired protein structure. It is within the scope of reaction design to, for example, mix a specific combination of a plurality of expression templates first, incubate the mixture for a certain period of time, and then add a preincubation liquid containing the other expression templates. This is because of the following reason. At the time of a translation reaction, an expression template-ribosome complex state (polysome) is formed first, and then the translation reaction proceeds. That is, the ease with which the polysome is formed varies depending on the sequence of the expression template, and hence, in simultaneous batch synthesis, sequence-dependently competing polysome formation is liable to occur. As a result, the quantitative balance of newly produced proteins is markedly biased, and a problem such as a markedly low yield of the complex is liable to occur.

In the wheat cell-free synthesis method, a protein can be synthesized from a plasmid having the promoter sequence of an SP6 or T7 RNA polymerase, a sequence for adding a 5' translation-promoting sequence, and a desired gene sequence, or a PCR product through use of a transcription/translation integrated expression kit (Premium One Expression kit manufactured by CellFree Sciences Co., Ltd.). When a protein complex is produced, simultaneous batch synthesis may be performed under a state in which, for example, plasmids having a plurality of gene sequences are mixed, but a higher complex synthesis yield can be obtained by, as described above, separately preincubating the plasmids to form polysomes and then further causing the translation reactions to proceed.

In addition, it is also one of the preferred modes of the present invention (this Example) to use a membrane protein as each of the proteins serving as the substance to be analyzed and the immobilized substance. The membrane protein may be synthesized in the form of a membrane protein-reconstituted liposome (proteoliposome) from any membrane protein expression template (mRNA) through use of ProteoLiposome Expression Kit manufactured by Cell-Free Sciences Co., Ltd. ProteoLiposome Expression Kit uses asolectin from soybeans, which is a complex lipid, as a lipid serving as a liposome source. This is because the formation of the proteoliposome is facilitated irrespective of the kind of the membrane protein. However, any liposomes formed of various lipids may be used depending on the kind of the membrane protein.

As a typical example, constituent lipids of cell membranes, such as phosphatidylcholines, sphingomyelin, phosphatidylethanolamines, phosphatidylserine, cholesterol, and triacylglycerols, may be used alone or as a mixture. In addition, any such lipid may be modified by, for example, biotinylation before being added, to thereby label the proteoliposome without modifying the protein.

When a protein having a disulfide bond in a molecule of the protein or between molecules thereof (in the case of the above-mentioned complex protein) is to be synthesized, disulfide bond formation may be achieved by appropriately controlling a reduction state at the time of the synthesis and utilizing the enzymatic oxidation process of, for example, a protein disulfide isomerase or endoplasmic reticulum oxidase 1.

(Proximity-Dependent Labeling Enzyme)

The inventors of the present invention have recognized that "when a protein, in particular, a non-denatured protein serving as the immobilized substance is immobilized on a substrate or an array, and the interaction between the immobilized substance and the substance to be analyzed is to be evaluated, a weak interaction is removed at the time of B/F separation, and hence an intermolecular interaction that originally exists cannot be detected." This fact has been found for the first time in the evaluation of a protein-protein interaction involving using an array having a non-denatured protein immobilized thereon.

In particular, intermolecular interactions each having a dissociation constant of $1\times10^{-8}$ M or more, which is weaker than an antibody-antigen reaction, are associated with the mechanisms of various physiological phenomena originating from intermolecular interactions, and are regarded as important targets for future drug discovery. For this reason, it is conceived that it is extremely important to detect weak intermolecular interactions with good sensitivity.

The term "proximity-dependent labeling enzyme" as used in the present invention refers to an enzyme having an ability to bind, to the immobilized substance, a molecule detectable as a marker (referred to as "labeling substance" in the present invention) when the substance to be analyzed and the immobilized substance on the array cause an intermolecular interaction and the immobilized substance is present in a proximity field of the proximity-dependent labeling enzyme bound to the substance to be analyzed.

The proximity-dependent labeling enzyme may be exemplified by an enzyme obtained by altering an existing enzyme to weaken its substrate specificity. For example, a transferase, a lyase, and a ligase are given as candidates therefor. As a method of weakening the substrate specificity, there is known, for example, a method involving converting or chemically modifying an amino acid, and examples thereof include the introduction of a mutation into a substrate-binding site and the introduction of the sequence of an allied enzyme.

The binding between the labeling substance and the protein serving as the immobilized substance is preferably stronger than the interaction between the substance to be analyzed and the immobilized substance, and is desirably covalent binding because the interaction is not eliminated at the time of B/F separation.

A fusion molecule obtained by binding the proximity-dependent labeling enzyme to the substance to be analyzed (substance to be analyzed that is labeled with a proximity-dependent labeling enzyme) is brought into contact with a non-denatured protein array, to thereby bind the labeling substance, with a covalent or firm binding force, to the protein serving as the immobilized substance on the protein array with which the substance to be analyzed that is labeled with a proximity-dependent labeling enzyme interacts. The labeling substance is substantially free from being eliminated or leaving from the immobilized substance even when undergoing the B/F separation step.

Further, after the washing, the labeling substance bound to the immobilized substance can be detected or quantified by a biochemical technique (e.g., mass spectrometry or electrophoresis).

A preferred proximity-dependent labeling enzyme of the present invention is a proximity-dependent biotin ligase obtained by altering part of the amino acid sequence of a BirA protein that is a biotin ligase of *Escherichia coli*. The BirA protein has a function of recognizing a specific amino acid sequence as a substrate and specifically binds biotin to a lysine residue in the amino acid sequence. Meanwhile, the proximity-dependent biotin ligase, having lost substrate specificity, has a function of binding biotin to lysine residues present on the surfaces of all substances including the immobilized substance in a proximity range.

Reported examples of the proximity-dependent biotin ligase include BioID (SEQ ID NO: 1), TurboID (SEQ ID NO: 2), and AirID (SEQ ID NO: 3) (Choi-Rhee., et al., Protein Sci, 2004 (Doi 10.1110/ps.04911804), Roux, K., et al., JCB, 2012 (Doi 10.1083/jcb.201112098), Branon, T C., et al., Nat Biotech, 2018 (Doi: 10.1038/nbt.4201), Kido, K., et al., eLife, 2020 (Doi 10.7554/eLife.54983)).

Further, suitable examples of the proximity-dependent biotin ligase include an AirID-S118G mutant (SEQ ID NO: 12), an AVVA-R118S mutant (SEQ ID NO: 13), an AVVA-R118G mutant (SEQ ID NO: 14), an AVVA-R118S,_Q141R mutant (SEQ ID NO: 15), and an AVVA-R118G,Q141R mutant (SEQ ID NO: 16).

According to the results of investigations made by the inventors of the present invention on various mutants of AVVA of the biotin ligase BirA of *Escherichia coli* (see eLife 2020; 9: e54983), an R118S or R118G mutation is preferred for the present invention, and an amino acid sequence around the R118 amino acid is desirably RG (R118S or R118G)RG. RG(R118S or R118G)RGR is more desired.

BioID has low biotin-labeling enzyme activity, and requires a reaction time (labeling time) of from 18 hours to 24 hours at a reaction temperature (labeling temperature) of 37° C. Meanwhile, TourboID has high activity, and requires a reaction time (labeling time) as short as 10 minutes at a reaction temperature (labeling temperature) of 26° C., but increases non-specific labeling.

Meanwhile, AirID, the AirID-S118G mutant, the AVVA-R118S mutant, and the AVVA-R118G mutant each require a reaction time (labeling time) of about 3 hours at a reaction temperature (labeling temperature) of 26° C., and cause extremely little non-specific labeling, and hence are the most suitable proximity-dependent biotin ligases. In addition, the inventors of the present invention have also found that further introduction of a Q141R mutation into an AVVA mutant (AVVA-R118S,Q141R mutant or AVVA-R118G, Q141R mutant) enhances its labeling activity.

An altered biotinylation enzyme to be used in the present invention is preferably any one or more of the following polypeptides:

(1) a polypeptide formed of an amino acid sequence set forth in SEQ ID NO: 1;
(2) a polypeptide formed of an amino acid sequence set forth in SEQ ID NO: 2;
(3) a polypeptide formed of an amino acid sequence set forth in SEQ ID NO: 3;
(4) a polypeptide formed of an amino acid sequence set forth in SEQ ID NO: 12;
(5) a polypeptide formed of an amino acid sequence set forth in SEQ ID NO: 13;
(6) a polypeptide formed of an amino acid sequence set forth in SEQ ID NO: 14;
(7) a polypeptide formed of an amino acid sequence set forth in SEQ ID NO: 15;
(8) a polypeptide formed of an amino acid sequence set forth in SEQ ID NO: 16;
(9) a polypeptide that has 1 to 10, 1 to 9, 1 to 8, 1 to 7, 1 to 6, 1 to 5, 1 to 4, 1 to 3, 1 or 2, or 1 amino acid substituted, deleted, inserted, and/or added in any one of the amino acid sequences set forth in SEQ ID NOS: 1 to 3 and 12 to 16, and that has substantially equivalent biotinylation enzyme activity to that of a polypeptide formed of any one of the amino acid sequences set forth in SEQ ID NOS: 1 to 3 and 13 to 16; and
(10) a polypeptide that has 90% or more, 91% or more, 92% or more, 93% or more, 94% or more, 95% or more, 96% or more, 97% or more, 98% or more, or 99% or more identity to any one of the amino acid sequences set forth in SEQ ID NOS: 1 to 3 and 12 to 16, and that has substantially equivalent biotinylation enzyme activity to that of a polypeptide formed of any one of the amino acid sequences set forth in SEQ ID NOS: 1 to 3 and 12 to 16.

The substantially equivalent biotinylation enzyme activity may be measured by a known method, and for example, a method used in Example 4 may be adopted. The activity may be higher or lower as compared to the biotinylation enzyme activity of the polypeptide formed of any one of the amino acid sequences set forth in SEQ ID NOS: 1 to 3 and 12 to 16. For example, the value of the comparison may be exemplified by 10%, 20%, 30%, 40%, 50%, 60%, 70%, 80%, 90%, 100%, 120%, 130%, 140%, 150%, 160%, 170%, 180%, 190%, 200%, 300%, 400%, 500%, 600%, 700%, 800%, 900%, or 1,000% or more.

In the introduction of a mutation into a peptide, for example, a substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable from the viewpoint of preventing basic properties (e.g., physical properties, function, physiological activity, or immunological activity) of the peptide from being changed.

The proximity-dependent labeling enzyme to be used in the present invention may be a genetically modified product or a chemically synthesized product. As long as a function is not impaired, a derivative or a fragment may be adopted, and an operation, such as modification, substitution, deletion, or addition, may be performed.

A preferred mode is a method involving preparing the substance to be analyzed and AirID as a fusion protein (AirID-labeled protein) by a genetic engineering technique on the basis of information on the base sequence of the protein serving as the substance to be analyzed and the base sequence of a gene encoding AirID. That is, the substance to be analyzed and AirID are prepared as a fusion protein by cloning a gene in which a gene encoding the substance to be analyzed and a gene encoding AirID are linked, and expressing the gene by a cell-free synthesis system.

The protein serving as the substance to be analyzed and AirID may be indirectly bound via a substance that binds to the substance to be analyzed (substance to be analyzed-supporting substance) to obtain AirID-substance to be analyzed-supporting substance-protein. In addition, a spacer may be inserted between AirID and the substance to be analyzed.

(Evaluation Method of the Present Invention)

An example of the evaluation method of the present invention is not particularly limited as long as the method includes: (1) a step of adding a substance to be analyzed that is labeled with a proximity-dependent modifying enzyme to an immobilized substance immobilized directly or indirectly on a substrate in the presence of a labeling substance; and (2) a step of detecting the labeling substance. A method involving using a non-denatured protein array as illustrated in FIG. 1 is exemplified below.

1) The immobilized substance is arranged and immobilized on the substrate. In this description, as a typical example, a non-denatured protein array using a non-denatured protein as the immobilized substance is used.

In order for the immobilized protein to keep a non-denatured state, the top of the array or the inside of the wells of the array is always filled with a buffer.

In order to prevent the protein immobilized on the magnetic beads from moving to an adjacent well together with the magnetic beads at the time of buffer change, it is preferred that the buffer be slowly removed from and put into the protein array. Particularly when the buffer is put thereinto, the buffer is desirably ejected toward a wall surface through use of a syringe or the like. Shaking of the protein array during the reaction and washing is desirably performed at such a shaking speed as to make about one to-and-fro motion per second in order to prevent the movement of the magnetic beads.

2) A storage buffer in the protein array is removed, and a fusion protein of AirID and the substance to be analyzed diluted with a reaction buffer is added into the protein array in the presence of biotin serving as a labeling substance. With regard to the addition, any method may be adopted as long as the immobilized substance and the substance to be analyzed can be brought into contact with each other. In addition, with regard to "in the presence of a labeling substance (biotin)," any method may be adopted as long as the immobilized substance and the labeling substance (biotin) can be brought into contact with each other. For example, the labeling substance may be added to the array at any of the following stages: before the addition of the substance to be analyzed to the array, simultaneous with the addition, or after the addition. The "storage buffer" means a near-neutral buffer suited for a biological reaction containing glycerol or the like for preventing the aggregation of a protein or stabilizing the structure thereof, but is not particularly limited. The "reaction buffer" means a near-neutral buffer suited for a biological reaction containing: a blocking agent for preventing the substance to be analyzed from being non-specifically adsorbed onto the substrate or the immobilized substance; and the labeling substance (biotin) and an activation energy source (ATP) which are required for the reaction, but is not particularly limited. A "washing buffer" means a near-neutral buffer suited for a biological reaction containing a salt or a surfactant for removing the substance to be analyzed that is free in the solution or is bound to the substrate or the immobilized substance, but is not particularly limited.

When, in the presence of biotin (and ATP as required), all the protein serving as the immobilized substance immobilized on the array and the AirID-fused protein serving as the substance to be analyzed interact with each other, and the immobilized substance and the substance to be analyzed are bound to each other, AirID labels a lysine residue of the immobilized substance in a proximity range with biotin. When the fusion protein contains no lysine residue, the protein may be altered so as to contain a lysine residue as required.

3) In the related art, a complex of a protein serving as an immobilized substance and a substance to be analyzed that are interacting with each other is used for analysis, and hence the substance to be analyzed that is free in the reaction buffer or non-specifically adsorbed onto the protein serving as the immobilized substance is removed by a washing operation. In the washing operation, the substance to be analyzed interacting specifically but weakly is also removed.

Meanwhile, in the interaction evaluation method of the present invention, biotin bound to the protein serving as the immobilized substance immobilized on the array is detected. Accordingly, even when the substance to be analyzed interacting specifically but weakly is removed by the washing operation, the interaction can be detected.

4) Biotin with which the protein serving as the immobilized substance immobilized on the array after the washing is labeled is detected using a substance that specifically recognizes and binds to biotin, and an interaction analysis result is obtained as a measurement image.

Examples of the substance that specifically recognizes and binds to biotin, which is used for the detection of the interaction, include an anti-biotin antibody and streptavidin. Any such substance is desirably HRP-labeled, AP-labeled, or fluorescently labeled. The anti-biotin antibody or streptavidin is desirably subjected to a binding reaction with biotin by being placed in the protein array in a state of being diluted with the reaction buffer. After the reaction, washing needs to be performed to remove the free anti-biotin antibody or streptavidin. After the washing, when an HRP/AP-labeled product is used, a chemiluminescence reagent is added, and luminescence obtained through a reaction between the chemiluminescence reagent and HRP/AP is measured with a detector for luminescence. An example of the detector for luminescence is LAS (manufactured by GE Healthcare). When fluorescent labeling is used, measurement is performed with a detector for fluorescence. An example of the detector for fluorescence is Typhoon (manufactured by GE Healthcare).

5) The presence or absence of the interaction between each protein serving as the immobilized substance on the array and the protein serving as the substance to be analyzed is determined from the measurement image.

For the determination of the interaction, it is desired that the signal of each spot on the measurement image be converted into a numerical value and a certain or higher value is determined as indicating the presence of the interaction. Analytical software such as Array-Pro Analyzer is desirably used for converting the measurement image into a numerical value. Thus, strengths (binding strengths) with which a plurality of immobilized substances and the substance to be analyzed interact can be measured at once.

(Binding Strength Measurement Capacity in Evaluation Method of the Present Invention)

The evaluation method of the present invention has been able to measure binding between TP53 and MDM2 in Examples described below.

In the literature "Mol Cancer Res 2003; 1: 1001-1008", it is reported that a dissociation constant between a TP53 peptide and MDM2 is from $6\times10^{-8}$ M to $7\times10^{-7}$ M with reference to literatures in which measurement is performed by isothermal titration calorimetry, a stopped-flow method, a fluorescence polarization measurement method, and the like.

In the literature "J. Biol. Chem. 2005, 280: 38795-38802", it is reported that a dissociation constant between TP53 (turn II motif) and MDM2 is $2\times10^{-5}$ M as measured by SPR.

In general, the dissociation constant between TP53 and MDM2 varies depending on various conditions, but is known to range from $6\times10^{-8}$ M to $2\times10^{-5}$ M as previously reported.

That is, the evaluation method of the present invention is capable of measuring binding having a dissociation constant of $1\times10^{-8}$ M or more, $1\times10^{-7}$ M or more, $1\times10^{-6}$ M or more, $1\times10^{-5}$ M or more, $1\times10^{-4}$ M or more, $1\times10^{-3}$ M or more, $1\times10^{-2}$ M or more, from $1\times10^{-8}$ M to $1\times10^{-3}$ M, from $1\times10^{-8}$ M to $1\times10^{-4}$ M, from $1\times10^{-8}$ M to $1\times10^{-5}$ M, from $1\times10^{-7}$ M to $1\times10^{-3}$ M, from $1\times10^{-7}$ M to $1\times10^{-4}$ M, from $1\times10^{-7}$ M to $1\times10^{-5}$ M, from $1\times10^{-6}$ M to $1\times10^{-3}$ M, from $1\times10^{-6}$ M to $1\times10^{-4}$ M, from $1\times10^{-6}$ M to $1\times10^{-5}$ M, from $1\times10^{-5}$ M to $1\times10^{-4}$ M, or from $6\times10^{-8}$ M to $2\times10^{-5}$ M.

(Binding Recruiter)

A binding recruiter in the present invention is not particularly limited as long as the binding recruiter is a substance capable of, for example, inducing, promoting, or initiating the interaction between the immobilized substance and the substance to be analyzed that is labeled with a proximity-dependent modifying enzyme, and examples thereof may include proteins, antibodies, nucleic acids (including DNA, RNA, and the like), peptides, low-molecular-weight compounds, medium-molecular-weight compounds, cell extracts, tissue extracts, saccharides, lipids, physiologically active substances, and complexes thereof.

Specifically, a thalidomide derivative or the like may be given as an example of a substance that recruits an interaction between CRBN and IKZF1 or SALL4 as described in Example 3.

Example 1

(Production of Non-Denatured Protein Array)

In Example 1 of the present invention, a non-denatured protein array was produced. Details are as described below.

(Synthesis of Protein serving as Immobilized Substance by Wheat Cell-free Synthesis System)

In non-denatured protein arrays to be used in Examples 2 and 3 and Comparative Example 1 of the present invention, proteins serving as immobilized substances were synthesized by a wheat cell-free synthesis system. The synthesized proteins serving as the immobilized substances were each kept under a solution from immobilization on the protein array to storage.

Template DNA for the synthesis of each immobilized substance was prepared by a PCR method. The template was synthesized by fusing a FLAG™ tag protein to be used for the measurement of a protein amount and a GST protein for binding to magnetic beads each having glutathione bound to the surface thereof (glutathione magnetic beads). The synthesized PCR product for each immobilized substance was subjected to a transcription reaction and then a translation reaction in a separate container (individual well of a microplate) to synthesize each immobilized substance. In the translation reaction, a wheat extract solution from which wheat-derived endogenous proteins capable of specifically binding to the glutathione magnetic beads had been removed was used (references: U.S. Pat. No. 7,838,640 B2 and U.S. Pat. No. 7,919,597 B2).

(Binding of GST Protein to Magnetic Beads and Purification)

The glutathione magnetic beads were added to the reaction liquid containing the wheat germ extract solution containing the protein serving as the immobilized substance after protein synthesis (after translation), and a binding reaction of the immobilized substance to the magnetic beads (GST-binding capacity: 10 mg/mL) via the GST protein was performed under stirring. After the binding reaction, while the magnetic beads were held in the container with a magnet, an unbound protein solution fraction containing a group of proteins derived from the wheat germ extract solution was removed.

A washing buffer was added into the container, the magnetic beads having the immobilized substance bound thereto were washed, and while the magnetic beads were held in the container with a magnet, the buffer after the washing was removed. This washing step was performed a plurality of times, and then a fresh washing buffer was added to prepare a suspended solution of the magnetic beads.

(Immobilization of Magnetic Beads on Array Substrate)

An amount of the magnetic bead suspension to be immobilized on an array substrate was aspirated with a dispensing apparatus, and dispensed at a designated position (well) on the substrate. The substrate used was obtained by fitting a magnet plate containing permanent magnets under a plate made of a resin having formed therein wells for holding the magnetic beads at designated positions (well plate).

(Storage of Array Substrate after Magnetic Bead Immobilization)

The array substrate used was made of a material free from breakage at low temperature so as to enable the produced protein array to be stored under ultra-low temperature. In addition, the array substrate used was produced from a material having no autofluorescence so as to enable signal detection through fluorescent labeling. As the permanent magnets of the magnet plate, there were used ones having a magnetic force enough to prevent the magnetic beads on the substrate from moving during the step of the interaction reaction between the immobilized substance and the substance to be analyzed on the array substrate.

After the dispensation and immobilization of the magnetic beads having bound thereto the protein serving as the immobilized substance, a buffer suited for the storage of the protein (buffer containing a reagent for protecting the protein) was added onto the array substrate, and the resultant was sealed and stored at −80° C. until use.

Figure 2:
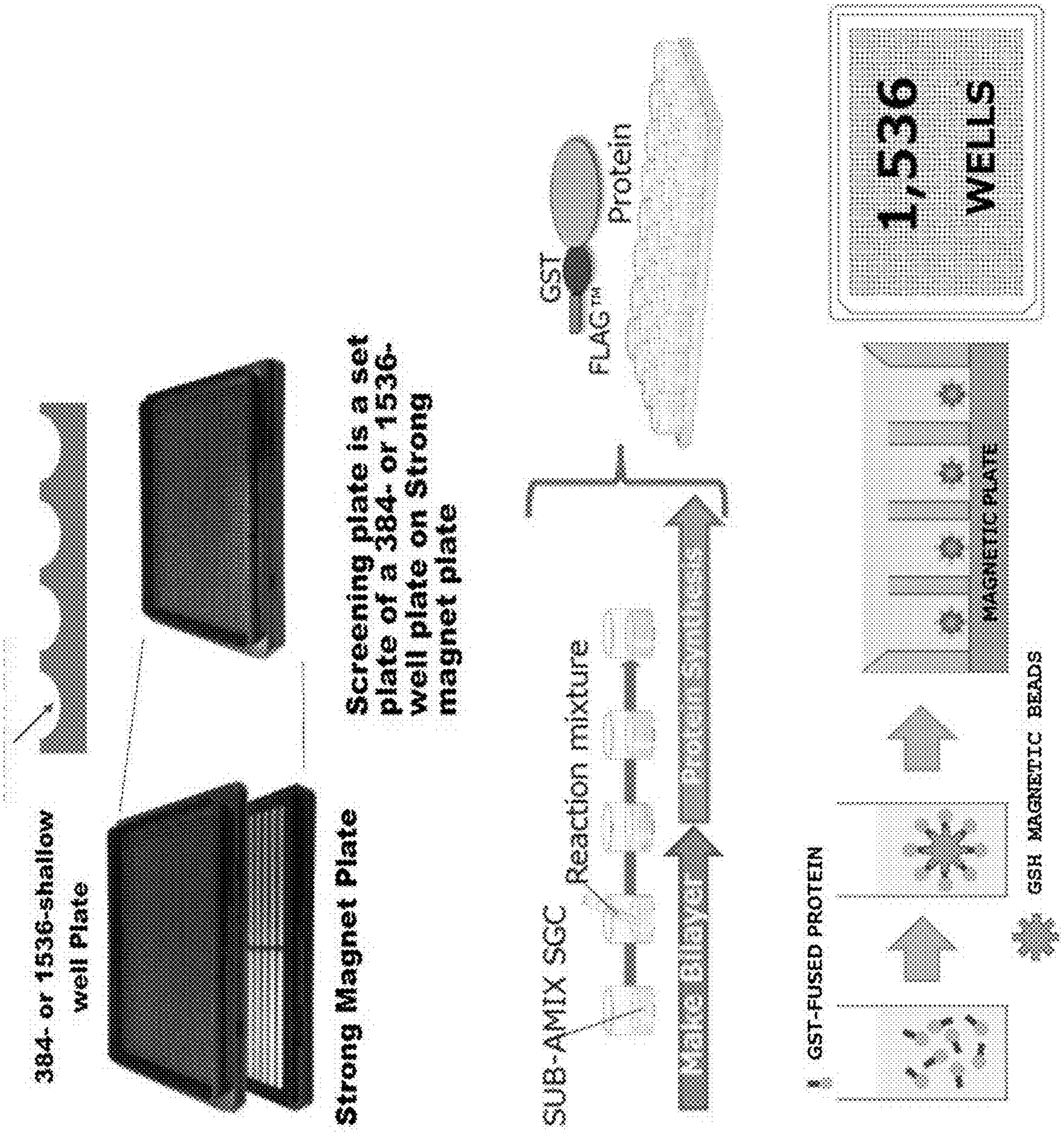
FIG. 2 is an illustration of an example of the production of a non-denatured protein array.

An illustration of the configuration of the protein array and an illustration of the flow of the immobilization of the protein serving as the immobilized substance are illustrated in FIG. 2.

Example 2

(Analysis of Intermolecular Interaction between TP53 and MDM2 or between Iκβα and RelA)

Figure 3:
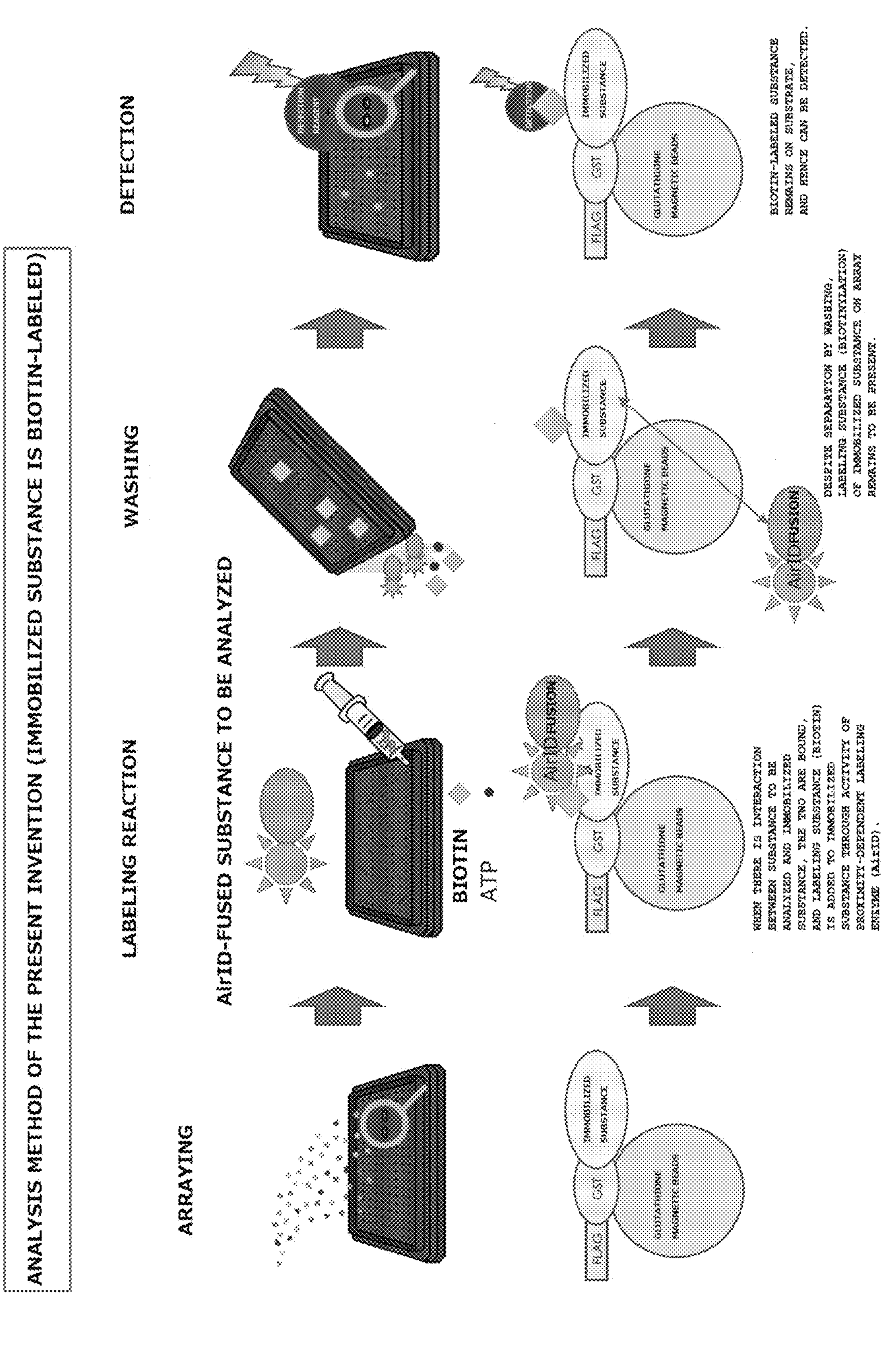
FIG. 3 is an illustration of the steps of an analysis method of Examples of the present invention.

In this Example, an interaction between TP53 and MDM2 or between Iκβα and RelA as proteins known to bind to each other was analyzed. The flow of this Example is illustrated in FIG. 3. Details are as described below.

(Protein Synthesis of Substance to be Analyzed and Immobilized Substance)

As a substance to be analyzed, template DNA in which TP53 (SEQ ID NO: 4) or Iκβα (SEQ ID NO: 5) was fused to AirID (SEQ ID NO: 3) was synthesized. As an immobilized substance (target protein), template DNA in which MDM2 (SEQ ID NO: 10), RelA (SEQ ID NO: 11), or any one of 10 kinds of proteins (controls) for comparison was fused to a FLAG™ tag protein and a GST protein was synthesized.

The synthesized template DNAs were used to synthesize AirID-fused substances to be analyzed and FLAG™-GST-fused immobilized substances through use of a wheat cell-free expression system.

(Binding of Immobilized Substance to Magnetic Beads and Purification)

The FLAG™-GST-fused immobilized substance (MDM2 or RelA, or any one of the other 10 kinds of proteins) was bound to glutathione magnetic beads to be used for a non-denatured protein array (GST-binding capacity: 10 mg/mL), followed by purification. For the magnetic beads after the purification, 15 nL (upper row of FIG. 4) or 75 nL (lower row of FIG. 4) of the magnetic beads were diluted to a 10 vol % slurry, quantitatively dispensed and arranged, and immobilized by the magnetic force of the magnet plate. Thus, a non-denatured protein array was produced.

(Biotin Labeling of Immobilized Substance in Presence of Substance to be analyzed)

The AirID-fused substance to be analyzed (Iκβα or TP53) diluted with a reaction buffer containing biotin and ATP was allowed to react with the FLAG™-GST-fused immobilized substance (MDM2 or RelA, or any one of the other 10 kinds of proteins) on the magnetic beads to perform biotin labeling of the FLAG™-GST-fused immobilized substance.

(Removal of Substance to be Analyzed)

In order to remove the AirID-fused substance to be analyzed that was free in the reaction buffer or adsorbed onto the magnetic beads, the reaction buffer was removed and then washing was performed a plurality of times with a washing buffer.

(Biotin Detection with HRP-Labeled Streptavidin)

The washing buffer was removed, and an HRP-labeled streptavidin solution diluted with the reaction buffer was added and allowed to react with the FLAG™-GST-fused immobilized substance on the magnetic beads. In order to remove free streptavidin, the reaction buffer was removed and then washing was performed a plurality of times with a washing buffer. After the removal of the washing buffer, a chemiluminescence reagent was added and subjected to a reaction. The resultant luminescence was detected with LAS4000 (manufactured by GE Healthcare) to provide measurement images.

(Results of Biotin Detection)

Figure 4:
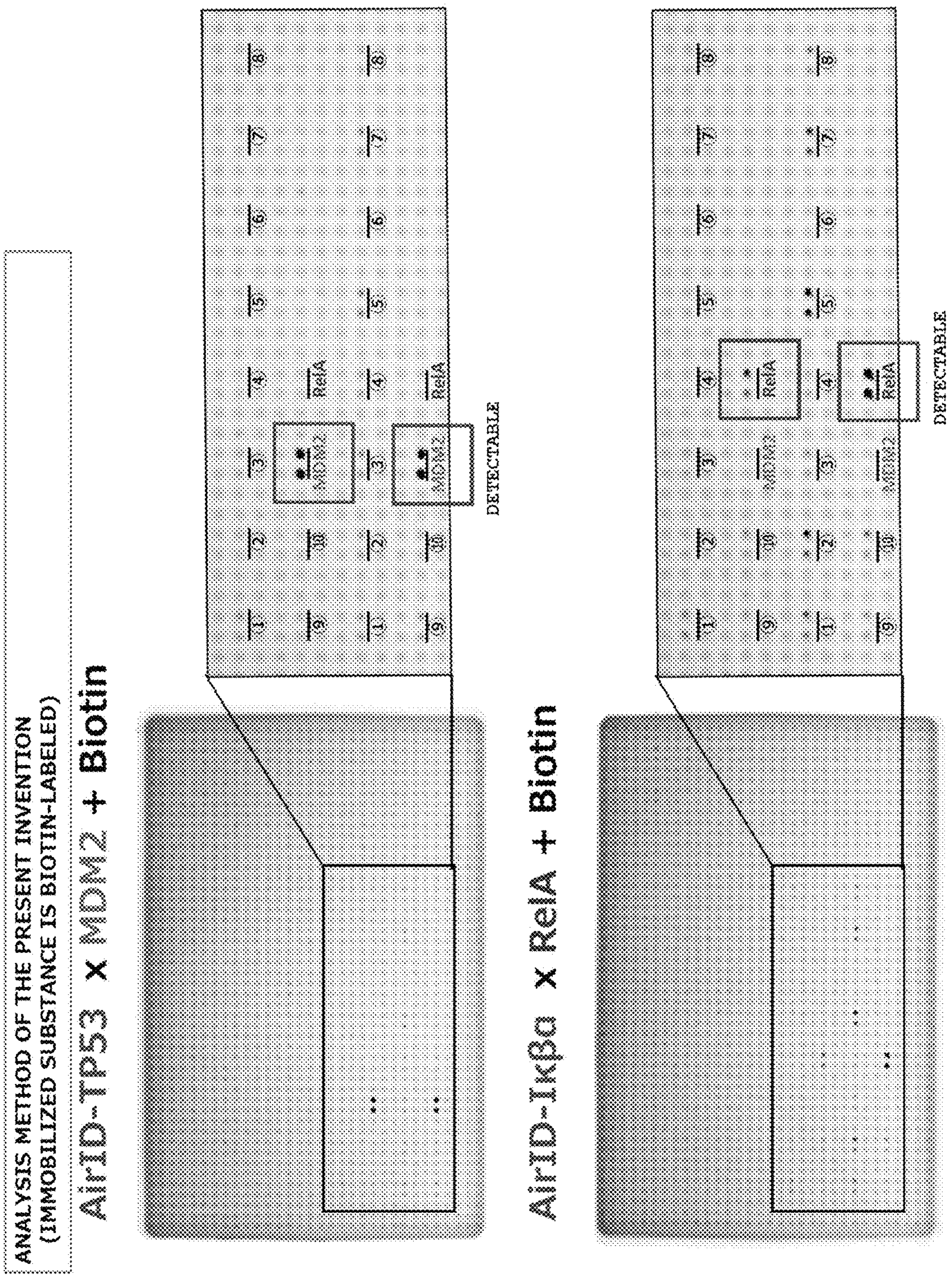
FIG. 4 shows results of Example 2.

The obtained measurement images are shown in FIG. 4.

Luminescence was recognized both between TP53 and MDM2, and between Iκβα and RelA. Luminescence was not recognized between the other proteins. In this Example, it was recognized that the analysis method of the present invention was capable of analyzing a specific interaction between the immobilized substance and the substance to be analyzed.

Example 3

(Analysis of Compound-dependent Interaction between CRBN and IKZF1 or SALL4)

In this Example, an interaction between proteins known to bind to each other, CRBN (SEQ ID NO: 7) and IKZF1 (SEQ ID NO: 6) or SALL4 (SEQ ID NO: 9), was analyzed. A thalidomide derivative (Pomalidomide) is known to enhance their binding. In view of this, the compound (thalidomide derivative) was added to a buffer to be used for a reaction to analyze how CRBN interacted with IKZF1 or SALL4 in a compound-dependent (binding recruiter) manner. The flow of this Example is illustrated in FIG. 3.

(Protein Synthesis of Substance to be Analyzed and Immobilized Substance)

As a substance to be analyzed (protein), template DNA in which CRBN was fused to AirID and template DNA in which a mutant CRBN (SEQ ID NO: 8) having a mutation introduced into its binding site for the thalidomide derivative was fused to AirID were synthesized. As an immobilized substance (protein), template DNA was synthesized by fusing IKZF1, SALL4, or Venus (control) for comparison to a FLAG™ tag protein and a GST protein.

The synthesized template DNAs were used to synthesize AirID-fused substances to be analyzed and FLAG™-GST-fused immobilized substances through use of a wheat cell-free expression system.

(Binding of Immobilized Substance to Magnetic Beads and Purification)

The FLAG™-GST-fused immobilized substance (IKZF1, SALL4, or Venus) was bound to glutathione magnetic beads, followed by purification. The magnetic beads after the purification were dispensed and arranged on the wells of the plate, and immobilized by the magnetic force of the magnet plate. Thus, a non-denatured protein array was produced.

(Biotin Labeling of Immobilized Substance in Presence of Substance to be Analyzed)

The AirID-fused substance to be analyzed (CRBN or mutant CRBN) diluted with a reaction buffer containing biotin and ATP was allowed to react with the FLAG™-GST-fused immobilized substance (IKZF1, SALL4, or Venus) on the magnetic beads to perform biotin labeling of the FLAG™-GST-fused immobilized substance.

(Removal of Substance to be Analyzed)

In order to remove the AirID-fused substance to be analyzed that was free in the reaction buffer or adsorbed onto the magnetic beads, the reaction buffer was removed and then washing was performed a plurality of times with a washing buffer.

(Biotin Detection with HRP-Labeled Streptavidin)

The washing buffer was removed, and an HRP-labeled streptavidin solution diluted with the reaction buffer was added and allowed to react with the FLAG™-GST-fused immobilized substance on the magnetic beads. In order to remove free streptavidin, the reaction buffer was removed and then washing was performed a plurality of times with a washing buffer. After the removal of the washing buffer, a chemiluminescence reagent was added and subjected to a reaction. The resultant luminescence was detected with LAS4000 (manufactured by GE Healthcare) to provide measurement images.

(Results of Biotin Detection)

Figure 5:
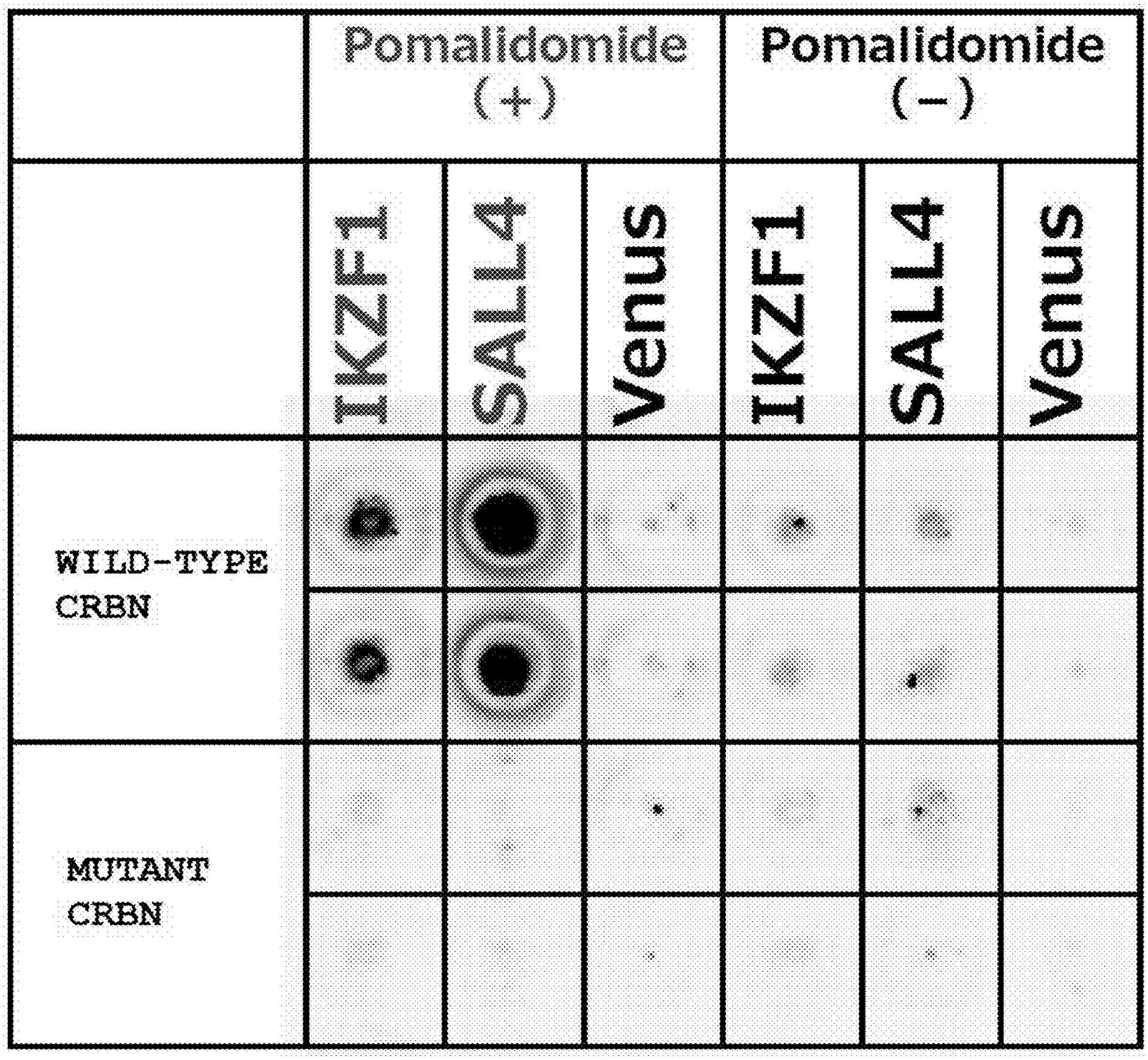
FIG. 5 shows results of Example 3.

The obtained measurement images are shown in FIG. 5.

The luminescence intensity of CRBN and IKZF1 or SALL4 was particularly increased under the condition that the compound was added. Meanwhile, hardly any increase in luminescence intensity was found under the condition that the compound was not added or the condition that the mutant CRBN having a mutation introduced into its binding site for the compound was used. In this Example, a compound-dependent interaction was able to be analyzed between CRBN and IKZF1 or SALL4.

That is, it was recognized that the analysis method of the present invention was capable of not only analyzing a specific interaction between the protein serving as the immobilized substance and the protein serving as the substance to be analyzed, but also analyzing a compound-dependent interaction.

Example 4

(Comparison of Altered Biotinylation Enzymes)

In this Example, various altered biotinylation enzymes were evaluated by the method used in Example 2.

Specifically, by a method similar to that for AirID (SEQ ID NO: 3) in Example 2, the interaction between TP53 and MDM2 or between Iκβα and RelA was analyzed using BioID (SEQ ID NO: 1), TurboID (SEQ ID NO: 2), an AirID-S118G mutant (SEQ ID NO: 12), an AWA-R118S mutant (SEQ ID NO: 13), an AVVA-R118G mutant (SEQ ID NO: 14), an AWA-R118S, Q141R mutant (SEQ ID NO: 15), and an AVVA-R118G, Q141R mutant (SEQ ID NO: 16).

The results of this Example including the results of Example 2 are shown in FIG. 8 and FIG. 9.

The results in the figures were standardized in that the dispensation amount of the magnetic beads on the wells of the plate was 75 nL. An exposure time at the time of luminescence detection with LAS4000 (manufactured by GE Healthcare) was set to 3 minutes for TurboID, and 10 minutes for the protein of any other sequence identification number. A signal value was obtained from a measurement image through use of Array-Pro Analyzer™.

According to the results in the figures, TurboID can perform labeling within a short period of time at ordinary temperature and has a high signal intensity, providing a sufficiently large contrast with a negative, but a certain signal (non-specific) is found even for an interaction that should be negative. Although measurement can be performed with a sufficiently high S/N value under the condition of a labeling time of 30 minutes, the signal intensity for a negative is increased to reduce the S/N value under the condition of a labeling time of 1 hour. Accordingly, the exposure time needs to be controlled.

BioID has low non-specificity, but has lower biotin modification activity than the other enzymes, requiring a high labeling temperature of 37° C. and a long labeling time (24 hours), and hence is not preferred for the evaluation of an interaction of a protein that is liable to be denatured or degraded.

The proximity-dependent biotin ligases that are AirID (SEQ ID NO: 3), the AirID-S118G mutant (SEQ ID NO: 12), the AWA-R118S mutant (SEQ ID NO: 13), the AVVA-R118G mutant (SEQ ID NO: 14), the AWA-R118S, Q141R mutant (SEQ ID NO: 15), and the AVVA-R118G, Q141R mutant (SEQ ID NO: 16) each require a labeling time as short as 3 hours and a relatively mild temperature as well, and also have extremely high specificity, and hence are preferred for use in the evaluation method of this Example.

Example 5

(Use of Membrane Protein as Immobilized Substance)

In this Example, a membrane protein was used as an immobilized substance.

As the immobilized substance, a cell surface antigen gene T1R1 (reference: Production of monoclonal antibodies against GPCR using cell-free synthesized GPCR antigen and biotinylated liposome-based interaction assay. Sci Rep. 5, 11333) was subcloned into a wheat cell-free expression vector (pEU-E01-His-MCS-N) manufactured by CellFree Sciences Co., Ltd., and synthesis was performed using ProteoLiposome Kit manufactured by CellFree Sciences Co., Ltd.

T1R1 is synthesized in a state (Proteo-liposome) in which most thereof is fitted in a lipid bilayer of asolectin liposomes in a Wepro7240 extract solution. This T1R1 synthesized crude liquid was mixed with Magnehis-ni-particles manufactured by Promega suspended in a phosphate buffer containing 0.5% of Tween 20 (surfactant) (final concentration of particles: 10%) to bind a T1R1-lipid complex to the magnetic beads via a His-tag. After buffer washing, the resultant was quantitatively dispensed in an amount corresponding to 15 nL in terms of the magnetic beads on the wells of the magnet plate to produce a non-denatured protein array. An anti-T1R1 antibody was used as a substance to be analyzed.

N-Protein A-AVVA R118S obtained by fusing Protein A to the N-terminal side of a proximity-dependent modifying enzyme (AVVA-R118S mutant (SEQ ID NO: 13)) was brought into contact with the anti-T1R1 antibody, and thus the proximity-dependent modifying enzyme was able to be simply bound to the Fc region of the antibody. A similar method was employed to produce cell surface antigen genes CXCR4, CD63, DRD1, GHSR, and PTGER1 as the immobilized substances, and anti-DRD1-AWA R118S as the substance to be analyzed, and the specificity of the antibody for each antigen was evaluated on the non-denatured protein array.

Figure 10:
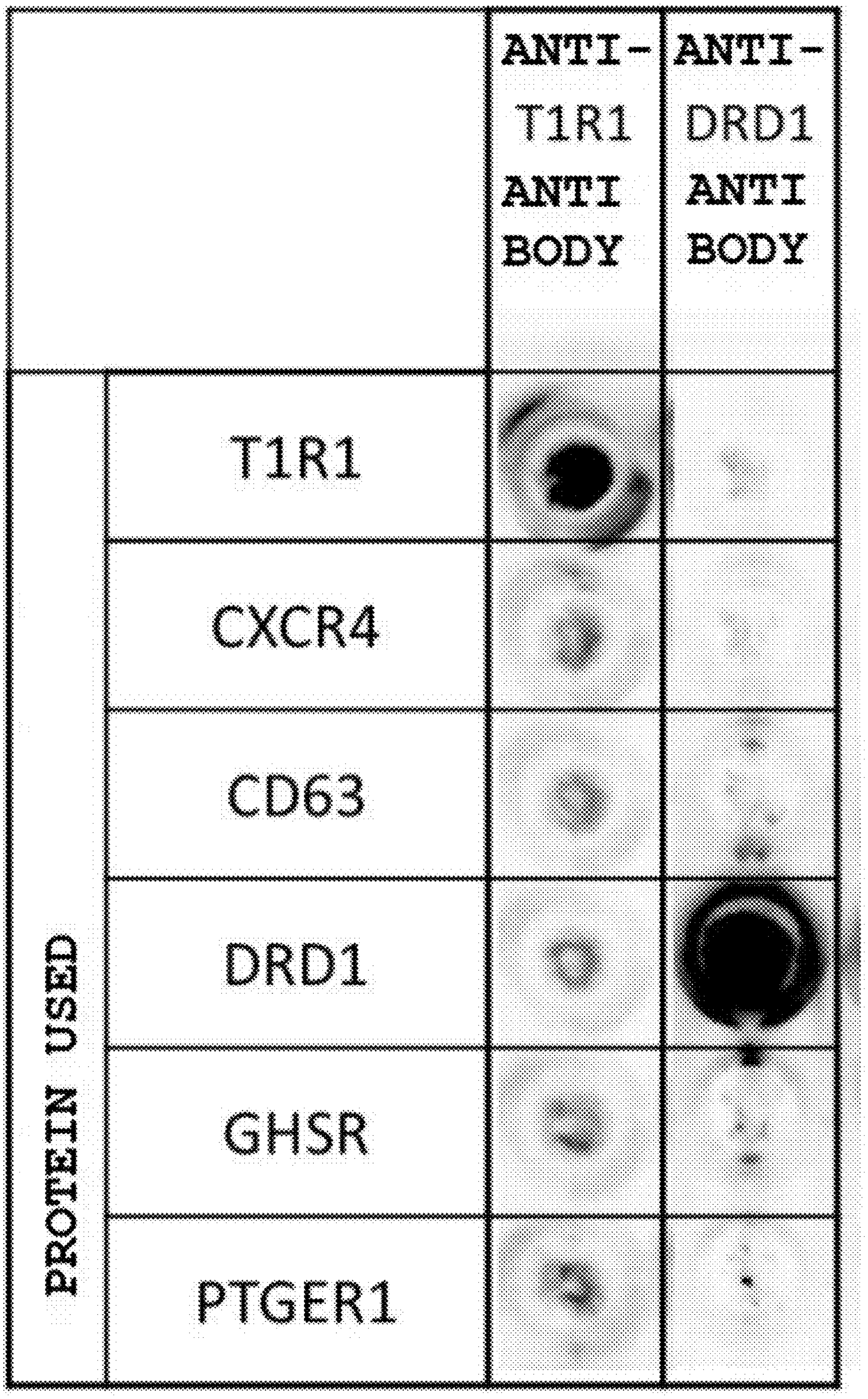
FIG. 10 shows results of Example 5.

The results of this Example are shown in FIG. 10.

It was recognized that the evaluation method of this Example was able to be utilized for analyzing the membrane protein serving as the immobilized substance simply, highly sensitively, and highly specifically.

Comparative Example 1

(Comparison to Related-Art Intermolecular Interaction Evaluation Method)

A related-art intermolecular interaction evaluation method was performed using as a model the analysis of the interactions between TP53 and MDM2, and between Iκβα and RelA.

Figure 6:
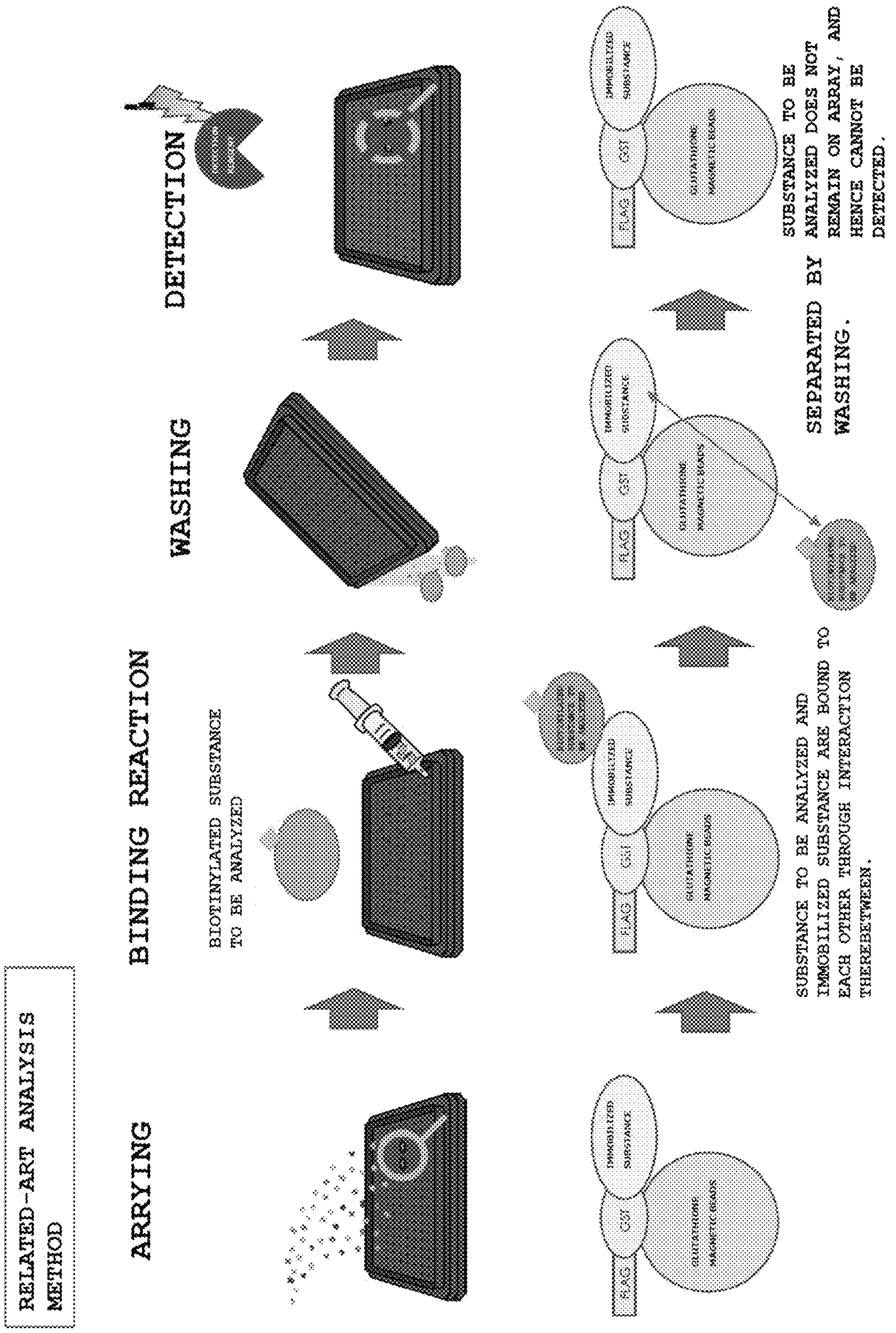
FIG. 6 is an illustration of the steps of a related-art analysis method.

In the related-art intermolecular interaction evaluation method, a substance to be analyzed (protein) is biotin-labeled, and its interaction with an immobilized substance (protein) is directly analyzed using biotin on the substance to be analyzed as an indicator. In that case, when the interaction between the substance to be analyzed and the immobilized substance is weak, and the substance to be analyzed is removed from the immobilized substance, despite the interaction, owing to a washing operation in the process of analysis, it is impossible to detect the interaction (see FIG. 6). In the related-art intermolecular interaction evaluation method, TP53 or Iκβα labeled with biotin by BirA was used.

(Preparation of Target Protein Used in Related-Art Intermolecular Interaction Analysis Method)

The substance to be analyzed used in the related-art intermolecular interaction analysis method was prepared as follows: a template for wheat cell-free expression was prepared, TP53 or Iκβα was fused as the substance to be analyzed to a BirA recognition sequence, and the protein was synthesized from the synthesized template through use of a cell-free protein synthesis method, followed by biotin labeling using BirA.

(Preparation of Immobilized Substance)

As the immobilized substance (protein) used in the related-art intermolecular interaction analysis method, MDM2, RelA, or any one of 10 kinds (controls) of proteins for comparison were synthesized as a FLAG™-GST protein-fused immobilized substance through use of the cell-free protein synthesis method.

(Binding of Immobilized Substance to Magnetic Beads and Purification)

The FLAG™-GST fusion protein (MDM2 or RelA, or any one of the other 10 kinds of proteins) prepared as the immobilized substance was bound to glutathione magnetic beads, followed by purification. The magnetic beads after the purification were dispensed and arranged on the wells of the plate, and immobilized by the magnetic force of the magnet plate. Thus, a non-denatured protein array was able to be produced.

(Biotin Labeling of Immobilized Substance in Presence of Substance to be analyzed)

In the related-art intermolecular interaction analysis method, the biotin-labeled fusion protein (TP53 or Iκβα) prepared as the substance to be analyzed was diluted with a reaction buffer, and allowed to react with the FLAG™-GST fusion protein (MDM2 or RelA, or any one of the other 10 kinds of proteins) on the magnetic beads.

(Removal of Substance to be Analyzed)

In order to remove the biotin-labeled fusion target protein that was free in the reaction buffer or adsorbed onto the magnetic beads, the reaction buffer was removed and then washing was performed a plurality of times with a washing buffer.

(Biotin Detection with HRP-Labeled Streptavidin)

The washing buffer was removed, and HRP-labeled streptavidin diluted with the reaction buffer was added and allowed to react with the FLAG™-GST-fused protein on the magnetic beads. In order to remove free streptavidin, the reaction buffer was removed and then washing was performed a plurality of times with a washing buffer. After the removal of the washing buffer, a chemiluminescence reagent was added and subjected to a reaction. The resultant luminescence was detected with LAS4000 (manufactured by GE Healthcare) to provide measurement images.

(Results of Biotin Detection)

Figure 7:
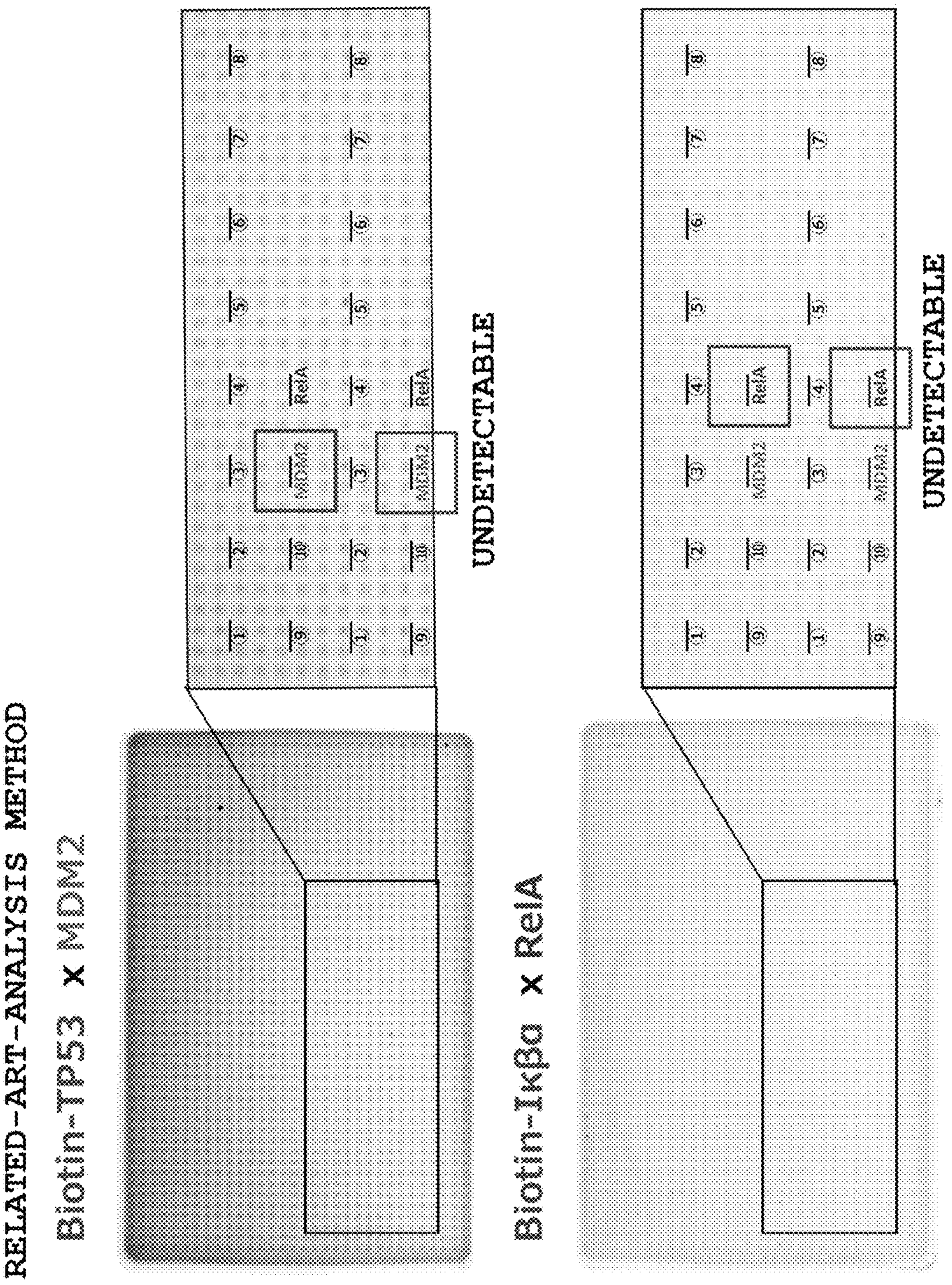
FIG. 7 shows results of Comparative Example 1.

The measurement images obtained by the related-art intermolecular interaction analysis method are shown in FIG. 7.

In the related-art analysis method, in which TP53 or Iκβα labeled with biotin instead of fusion with AirID was used, an increase in luminescence intensity was unable to be recognized. Meanwhile, in Example 2 employing the analysis method of the present invention, luminescence was recognized both between TP53 and MDM2, and between Iκβα and RelA. Luminescence was not recognized between the other proteins.

Thus, the analysis method using the related-art protein array failed to detect interactions between TP53 and MDM2, and between Iκβα and RelA. A conceivable reason for the detection failure is that, in the washing step, the intermolecular interaction between the proteins was removed, and the biotin-labeled substance to be analyzed (TP53 or Iκβα) was washed away.

As apparent from the foregoing, the intermolecular interaction analysis method of the present invention is capable of analyzing a relatively weak intermolecular interaction unlike the related-art intermolecular interaction analysis method.

INDUSTRIAL APPLICABILITY

The evaluation method of the present invention is capable of detecting an interaction that has not been able to be detected by the related-art evaluation method.

The invention claimed is:

1. A method of evaluating an interaction between a protein serving as an immobilized substance indirectly immobilized on an array via magnetic bead and a substance to be analyzed that is labeled with a proximity-dependent biotin ligase comprising a mutation at position R118 of the BirA protein of *Escherichia coli*, which results in reduced substrate specificity, the method comprising the steps of:

(1) adding the substance to be analyzed that is labeled with the proximity-dependent biotin ligase to the immobilized substance indirectly immobilized on the array via magnetic bead in the presence of biotin; and (2) detecting the biotin.

2. The evaluation method according to claim 1, further comprising a step of washing the array between the step (1) and the step (2).

3. The evaluation method according to claim 1, wherein the interaction has a binding dissociation constant of $1\times10^{-8}$ M or more.

4. The evaluation method according to claim 1, wherein the immobilized substance is a protein in a solution.

5. The evaluation method according to claim 1, wherein the immobilized substance is a non-denatured protein.

6. The evaluation method according to claim 1, wherein the proximity-dependent biotin ligase is any one or more of the following polypeptides:

(1) a polypeptide formed of an amino acid sequence set forth in SEQ ID NO: 1;
(2) a polypeptide formed of an amino acid sequence set forth in SEQ ID NO: 2;
(3) a polypeptide formed of an amino acid sequence set forth in SEQ ID NO: 3;
(4) a polypeptide formed of an amino acid sequence set forth in SEQ ID NO: 12;
(5) a polypeptide formed of an amino acid sequence set forth in SEQ ID NO: 13;
(6) a polypeptide formed of an amino acid sequence set forth in SEQ ID NO: 14;
(7) a polypeptide formed of an amino acid sequence set forth in SEQ ID NO: 15; and
(8) a polypeptide formed of an amino acid sequence set forth in SEQ ID NO: 16.

7. The evaluation method according to claim 1, further comprising adding a binding recruiter.

8. The evaluation method according to claim 1,
wherein the immobilized substance is a membrane protein, and
wherein the substance to be analyzed is an antigen-binding substance.

9. A method of evaluating an interaction between a protein serving as an immobilized substance indirectly immobilized on an array via magnetic bead and a substance to be analyzed that is labeled with a polypeptide having 1 to 10 amino acids substituted, deleted, inserted and/or added in any one of the amino acid sequences set forth in SEQ ID NOs: 1 to 3 and 12 to 16, and having biotinylation enzyme activity, the method comprising the steps of:
(1) adding the substance to be analyzed that is labeled with the polypeptide to the immobilized substance indirectly immobilized on the array via magnetic bead in the presence of biotin; and
(2) detecting the biotin.

* * * * *

SEQUENCE LISTING

```
<160> NUMBER OF SEQ ID NOS: 16

<210> SEQ ID NO 1
<211> LENGTH: 321
<212> TYPE: PRT
<213> ORGANISM: Artificial Sequence
<220> FEATURE:
<223> OTHER INFORMATION: BioID

<400> SEQUENCE: 1

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
```

65 70 75 80

Val Ala Val Leu Pro Val Ile Asp Ser Thr Asn Gln Tyr Leu Leu Asp
85 90 95

Arg Ile Gly Glu Leu Lys Ser Gly Asp Ala Cys Ile Ala Glu Tyr Gln
100 105 110

Gln Ala Gly Arg Gly Gly Arg Gly Arg Lys Trp Phe Ser Pro Phe Gly
115 120 125

Ala Asn Leu Tyr Leu Ser Met Phe Trp Arg Leu Glu Gln Gly Pro Ala
130 135 140

Ala Ala Ile Gly Leu Ser Leu Val Ile Gly Ile Val Met Ala Glu Val
145 150 155 160

Leu Arg Lys Leu Gly Ala Asp Lys Val Arg Val Lys Trp Pro Asn Asp
165 170 175

Leu Tyr Leu Gln Asp Arg Lys Leu Ala Gly Ile Leu Val Glu Leu Thr
180 185 190

Gly Lys Thr Gly Asp Ala Ala Gln Ile Val Ile Gly Ala Gly Ile Asn
195 200 205

Met Ala Met Arg Arg Val Glu Glu Ser Val Val Asn Gln Gly Trp Ile
210 215 220

Thr Leu Gln Glu Ala Gly Ile Asn Leu Asp Arg Asn Thr Leu Ala Ala
225 230 235 240

Met Leu Ile Arg Glu Leu Arg Ala Ala Leu Glu Leu Phe Glu Gln Glu
245 250 255

Gly Leu Ala Pro Tyr Leu Ser Arg Trp Glu Lys Leu Asp Asn Phe Ile
260 265 270

Asn Arg Pro Val Lys Leu Ile Ile Gly Asp Lys Glu Ile Phe Gly Ile
275 280 285

Ser Arg Gly Ile Asp Lys Gln Gly Ala Leu Leu Leu Glu Gln Asp Gly
290 295 300

Ile Ile Lys Pro Trp Met Gly Gly Glu Ile Ser Leu Arg Ser Ala Glu
305 310 315 320

Lys

<210> SEQ ID NO 2
<211> LENGTH: 321
<212> TYPE: PRT
<213> ORGANISM: Artificial Sequence
<220> FEATURE:
<223> OTHER INFORMATION: TurboID

<400> SEQUENCE: 2

Met Lys Asp Asn Thr Val Pro Leu Lys Leu Ile Ala Leu Leu Ala Asn
1 5 10 15

Gly Glu Phe His Ser Gly Glu Gln Leu Gly Glu Thr Leu Gly Met Ser
20 25 30

Arg Ala Ala Ile Asn Lys His Ile Gln Thr Leu Arg Asp Trp Gly Val
35 40 45

Asp Val Phe Thr Val Pro Gly Lys Gly Tyr Ser Leu Pro Glu Pro Ile
50 55 60

Pro Leu Leu Asn Ala Lys Gln Ile Leu Gly Gln Leu Asp Gly Gly Ser
65 70 75 80

Val Ala Val Leu Pro Val Val Asp Ser Thr Asn Gln Tyr Leu Leu Asp
85 90 95

Arg Ile Gly Glu Leu Lys Ser Gly Asp Ala Cys Ile Ala Glu Tyr Gln
100 105 110

```
Gln Ala Gly Arg Gly Ser Arg Gly Arg Lys Trp Phe Ser Pro Phe Gly
        115                 120                 125

Ala Asn Leu Tyr Leu Ser Met Phe Trp Arg Leu Lys Arg Gly Pro Ala
    130                 135                 140

Ala Ala Ile Gly Leu Gly Pro Val Ile Gly Ile Val Met Ala Glu Ala
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Ala
            180                 185                 190

Gly Ile Thr Gly Asp Ala Ala Gln Ile Val Ile Gly Ala Gly Ile Asn
        195                 200                 205

Val Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Thr Leu Ile Arg Glu Leu Arg Ala Ala Leu Glu Leu Phe Glu Gln Glu
                245                 250                 255

Gly Leu Ala Pro Tyr Leu Pro Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Val Ile Lys Pro Trp Met Gly Gly Glu Ile Ser Leu Arg Ser Ala Glu
305                 310                 315                 320

Lys


<210> SEQ ID NO 3
<211> LENGTH: 319
<212> TYPE: PRT
<213> ORGANISM: Artificial Sequence
<220> FEATURE:
<223> OTHER INFORMATION: AirID

<400> SEQUENCE: 3

Met Lys Asp Asn Thr Val Pro Leu Thr Leu Ile Ser Ile Leu Ala Asp
1               5                   10                  15

Gly Glu Phe His Ser Gly Glu Gln Leu Gly Glu Gln Leu Gly Met Ser
            20                  25                  30

Arg Ala Ala Ile Asn Lys His Ile Lys Thr Leu Arg Asp Trp Gly Val
        35                  40                  45

Asp Val Phe Arg Val Gln Gly Lys Gly Tyr Cys Leu Pro Glu Pro Ile
    50                  55                  60

Gln Leu Leu Asp Glu Glu Lys Ile Arg Gln Gln Leu Asp Glu Gly Ser
65                  70                  75                  80

Val Thr Val Leu Pro Val Ile Asp Ser Thr Asn Gln Tyr Leu Leu Asp
                85                  90                  95

Arg Leu Asp Glu Leu Thr Ser Gly Asp Val Cys Ile Ala Glu Tyr Gln
            100                 105                 110

Gln Ala Gly Arg Gly Ser Arg Gly Arg Lys Trp Phe Ser Pro Phe Gly
        115                 120                 125

Ala Asn Leu Tyr Leu Ser Met Tyr Trp Arg Leu Glu Gln Gly Pro Ala
    130                 135                 140
```

```
Ala Ala Met Gly Leu Ser Leu Val Ile Gly Ile Val Met Ala Glu Thr
145                 150                 155                 160

Leu Gln Lys Leu Gly Ala Asp Gly Val Arg Val Lys Trp Pro Asn Asp
                165                 170                 175

Leu Tyr Leu Asn Asp Arg Lys Leu Ala Gly Ile Leu Val Glu Met Thr
            180                 185                 190

Gly Lys Thr Gly Asp Ala Ala His Ile Val Ile Gly Ala Gly Ile Asn
        195                 200                 205

Leu Ser Met Arg Glu Pro Glu Thr Asp Glu Val Asp Gln Ser Trp Ile
    210                 215                 220

Asn Leu Gln Glu Ala Gly Ile Thr Ile Asp Arg Asn Gln Leu Ala Ala
225                 230                 235                 240

Arg Leu Ile Lys Asp Leu Arg Ser Ala Leu Arg Gln Phe Glu Gln Gln
                245                 250                 255

Gly Leu Ala Pro Phe Leu Ser Arg Trp Glu Ala Leu Asp Asn Phe Ile
            260                 265                 270

Asn Arg Pro Val Lys Leu Ile Ile Gly Asp Arg Glu Ile His Gly Ile
        275                 280                 285

Ala Arg Gly Ile Asn Glu Gln Gly Ala Leu Leu Leu Glu Gln Asp Gly
    290                 295                 300

Val Ile Lys Pro Trp Ile Gly Gly Glu Ile Ser Leu Arg Ser Ala
305                 310                 315


<210> SEQ ID NO 4
<211> LENGTH: 393
<212> TYPE: PRT
<213> ORGANISM: Homo sapiens

<400> SEQUENCE: 4

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205
```

```
Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390


<210> SEQ ID NO 5
<211> LENGTH: 317
<212> TYPE: PRT
<213> ORGANISM: Homo sapiens

<400> SEQUENCE: 5

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp Ser Met Lys Asp Glu Glu Tyr Glu Gln Met Val Lys Glu
        35                  40                  45

Leu Gln Glu Ile Arg Leu Glu Pro Gln Glu Val Pro Arg Ser Ser Glu
    50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
```

```
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Phe Thr Glu Asp Glu Leu Pro
    290                 295                 300

Tyr Asp Asp Cys Val Phe Gly Gly Gln Arg Leu Thr Leu
305                 310                 315


<210> SEQ ID NO 6
<211> LENGTH: 519
<212> TYPE: PRT
<213> ORGANISM: Homo sapiens

<400> SEQUENCE: 6

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Thr Leu Tyr Pro Val Ile
225                 230                 235                 240
```

```
Lys Glu Glu Thr Asn His Ser Glu Met Ala Glu Asp Leu Cys Lys Ile
                245                 250                 255

Gly Ser Glu Arg Ser Leu Val Leu Asp Arg Leu Ala Ser Asn Val Ala
            260                 265                 270

Lys Arg Lys Ser Ser Met Pro Gln Lys Phe Leu Gly Asp Lys Gly Leu
        275                 280                 285

Ser Asp Thr Pro Tyr Asp Ser Ser Ala Ser Tyr Glu Lys Glu Asn Glu
    290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
                325                 330                 335

Gly Ser Glu Val Val Pro Val Ile Ser Pro Met Tyr Gln Leu His Lys
            340                 345                 350

Pro Leu Ala Glu Gly Thr Pro Arg Ser Asn His Ser Ala Gln Asp Ser
        355                 360                 365

Ala Val Glu Asn Leu Leu Leu Leu Ser Lys Ala Lys Leu Val Pro Ser
    370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
                405                 410                 415

His Ile Ala Pro His Ala Arg Asn Gly Leu Ser Leu Lys Glu Glu His
            420                 425                 430

Arg Ala Tyr Asp Leu Leu Arg Ala Ala Ser Glu Asn Ser Gln Asp Ala
        435                 440                 445

Leu Arg Val Val Ser Thr Ser Gly Glu Gln Met Lys Val Tyr Lys Cys
    450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser His Ile Thr Arg Gly
            500                 505                 510

Glu His Arg Phe His Met Ser
        515


<210> SEQ ID NO 7
<211> LENGTH: 442
<212> TYPE: PRT
<213> ORGANISM: Homo sapiens

<400> SEQUENCE: 7

Met Ala Gly Glu Gly Asp Gln Gln Asp Ala Ala His Asn Met Gly Asn
1               5                   10                  15

His Leu Pro Leu Leu Pro Ala Glu Ser Glu Glu Glu Asp Glu Met Glu
            20                  25                  30

Val Glu Asp Gln Asp Ser Lys Glu Ala Lys Lys Pro Asn Ile Ile Asn
        35                  40                  45

Phe Asp Thr Ser Leu Pro Thr Ser His Thr Tyr Leu Gly Ala Asp Met
    50                  55                  60

Glu Glu Phe His Gly Arg Thr Leu His Asp Asp Asp Ser Cys Gln Val
65                  70                  75                  80

Ile Pro Val Leu Pro Gln Val Met Met Ile Leu Ile Pro Gly Gln Thr
                85                  90                  95
```

```
Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
    130                 135                 140

Arg Glu Glu Gln Asp Phe Gly Ile Glu Ile Val Lys Val Lys Ala Ile
145                 150                 155                 160

Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
        195                 200                 205

Pro Ser Lys Pro Val Ser Arg Glu Asp Gln Cys Ser Tyr Lys Trp Trp
    210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
    290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
                325                 330                 335

Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
        355                 360                 365

Asn Leu Ile Gly Arg Pro Ser Thr Glu His Ser Trp Phe Pro Gly Tyr
    370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
            420                 425                 430

Ile Ser Pro Asp Lys Val Ile Leu Cys Leu
        435                 440
```

<210> SEQ ID NO 8
<211> LENGTH: 442
<212> TYPE: PRT
<213> ORGANISM: Artificial Sequence
<220> FEATURE:
<223> OTHER INFORMATION: CRBN mutant in which Y at position 384 and W at position 386 were replaced by A

<400> SEQUENCE: 8

```
Met Ala Gly Glu Gly Asp Gln Gln Asp Ala Ala His Asn Met Gly Asn
```

-continued

```
1               5                   10                  15

His Leu Pro Leu Leu Pro Ala Glu Ser Glu Glu Glu Asp Glu Met Glu
            20                  25                  30

Val Glu Asp Gln Asp Ser Lys Glu Ala Lys Lys Pro Asn Ile Ile Asn
        35                  40                  45

Phe Asp Thr Ser Leu Pro Thr Ser His Thr Tyr Leu Gly Ala Asp Met
    50                  55                  60

Glu Glu Phe His Gly Arg Thr Leu His Asp Asp Asp Ser Cys Gln Val
65                  70                  75                  80

Ile Pro Val Leu Pro Gln Val Met Met Ile Leu Ile Pro Gly Gln Thr
                85                  90                  95

Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
    130                 135                 140

Arg Glu Glu Gln Asp Phe Gly Ile Glu Ile Val Lys Val Lys Ala Ile
145                 150                 155                 160

Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
        195                 200                 205

Pro Ser Lys Pro Val Ser Arg Glu Asp Gln Cys Ser Tyr Lys Trp Trp
    210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
    290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
                325                 330                 335

Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
        355                 360                 365

Asn Leu Ile Gly Arg Pro Ser Thr Glu His Ser Trp Phe Pro Gly Ala
    370                 375                 380

Ala Ala Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
            420                 425                 430
```

```
Ile Ser Pro Asp Lys Val Ile Leu Cys Leu
        435                 440


<210> SEQ ID NO 9
<211> LENGTH: 1053
<212> TYPE: PRT
<213> ORGANISM: Homo sapiens

<400> SEQUENCE: 9

Met Ser Arg Arg Lys Gln Ala Lys Pro Gln His Ile Asn Ser Glu Glu
1               5                   10                  15

Asp Gln Gly Glu Gln Gln Pro Gln Gln Gln Thr Pro Glu Phe Ala Asp
            20                  25                  30

Ala Ala Pro Ala Ala Pro Ala Ala Gly Glu Leu Gly Ala Pro Val Asn
        35                  40                  45

His Pro Gly Asn Asp Glu Val Ala Ser Glu Asp Glu Ala Thr Val Lys
    50                  55                  60

Arg Leu Arg Arg Glu Glu Thr His Val Cys Glu Lys Cys Cys Ala Glu
65                  70                  75                  80

Phe Phe Ser Ile Ser Glu Phe Leu Glu His Lys Lys Asn Cys Thr Lys
                85                  90                  95

Asn Pro Pro Val Leu Ile Met Asn Asp Ser Glu Gly Pro Val Pro Ser
            100                 105                 110

Glu Asp Phe Ser Gly Ala Val Leu Ser His Gln Pro Thr Ser Pro Gly
        115                 120                 125

Ser Lys Asp Cys His Arg Glu Asn Gly Gly Ser Ser Glu Asp Met Lys
    130                 135                 140

Glu Lys Pro Asp Ala Glu Ser Val Val Tyr Leu Lys Thr Glu Thr Ala
145                 150                 155                 160

Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
            180                 185                 190

Val Asn Gln Arg Ser Ala Asp Ala Leu Pro Ala Pro Val Pro Gly Ala
        195                 200                 205

Asn Ser Ile Pro Trp Val Leu Glu Gln Ile Leu Cys Leu Gln Gln Gln
    210                 215                 220

Gln Leu Gln Gln Ile Gln Leu Thr Glu Gln Ile Arg Ile Gln Val Asn
225                 230                 235                 240

Met Trp Ala Ser His Ala Leu His Ser Ser Gly Ala Gly Ala Asp Thr
                245                 250                 255

Leu Lys Thr Leu Gly Ser His Met Ser Gln Gln Val Ser Ala Ala Val
            260                 265                 270

Ala Leu Leu Ser Gln Lys Ala Gly Ser Gln Gly Leu Ser Leu Asp Ala
        275                 280                 285

Leu Lys Gln Ala Lys Leu Pro His Ala Asn Ile Pro Ser Ala Thr Ser
    290                 295                 300

Ser Leu Ser Pro Gly Leu Ala Pro Phe Thr Leu Lys Pro Asp Gly Thr
305                 310                 315                 320

Arg Val Leu Pro Asn Val Met Ser Arg Leu Pro Ser Ala Leu Leu Pro
                325                 330                 335

Gln Ala Pro Gly Ser Val Leu Phe Gln Ser Pro Phe Ser Thr Val Ala
            340                 345                 350

Leu Asp Thr Ser Lys Lys Gly Lys Gly Lys Pro Pro Asn Ile Ser Ala
```

```
        355                 360                 365

Val Asp Val Lys Pro Lys Asp Glu Ala Ala Leu Tyr Lys His Lys Cys
    370                 375                 380

Lys Tyr Cys Ser Lys Val Phe Gly Thr Asp Ser Ser Leu Gln Ile His
385                 390                 395                 400

Leu Arg Ser His Thr Gly Glu Arg Pro Phe Val Cys Ser Val Cys Gly
                405                 410                 415

His Arg Phe Thr Thr Lys Gly Asn Leu Lys Val His Phe His Arg His
            420                 425                 430

Pro Gln Val Lys Ala Asn Pro Gln Leu Phe Ala Glu Phe Gln Asp Lys
        435                 440                 445

Val Ala Ala Gly Asn Gly Ile Pro Tyr Ala Leu Ser Val Pro Asp Pro
    450                 455                 460

Ile Asp Glu Pro Ser Leu Ser Leu Asp Ser Lys Pro Val Leu Val Thr
465                 470                 475                 480

Thr Ser Val Gly Leu Pro Gln Asn Leu Ser Ser Gly Thr Asn Pro Lys
                485                 490                 495

Asp Leu Thr Gly Gly Ser Leu Pro Gly Asp Leu Gln Pro Gly Pro Ser
            500                 505                 510

Pro Glu Ser Glu Gly Gly Pro Thr Leu Pro Gly Val Gly Pro Asn Tyr
        515                 520                 525

Asn Ser Pro Arg Ala Gly Gly Phe Gln Gly Ser Gly Thr Pro Glu Pro
    530                 535                 540

Gly Ser Glu Thr Leu Lys Leu Gln Gln Leu Val Glu Asn Ile Asp Lys
545                 550                 555                 560

Ala Thr Thr Asp Pro Asn Glu Cys Leu Ile Cys His Arg Val Leu Ser
                565                 570                 575

Cys Gln Ser Ser Leu Lys Met His Tyr Arg Thr His Thr Gly Glu Arg
            580                 585                 590

Pro Phe Gln Cys Lys Ile Cys Gly Arg Ala Phe Ser Thr Lys Gly Asn
        595                 600                 605

Leu Lys Thr His Leu Gly Val His Arg Thr Asn Thr Ser Ile Lys Thr
    610                 615                 620

Gln His Ser Cys Pro Ile Cys Gln Lys Lys Phe Thr Asn Ala Val Met
625                 630                 635                 640

Leu Gln Gln His Ile Arg Met His Met Gly Gly Gln Ile Pro Asn Thr
                645                 650                 655

Pro Leu Pro Glu Asn Pro Cys Asp Phe Thr Gly Ser Glu Pro Met Thr
            660                 665                 670

Val Gly Glu Asn Gly Ser Thr Gly Ala Ile Cys His Asp Asp Val Ile
        675                 680                 685

Glu Ser Ile Asp Val Glu Glu Val Ser Ser Gln Glu Ala Pro Ser Ser
    690                 695                 700

Ser Ser Lys Val Pro Thr Pro Leu Pro Ser Ile His Ser Ala Ser Pro
705                 710                 715                 720

Thr Leu Gly Phe Ala Met Met Ala Ser Leu Asp Ala Pro Gly Lys Val
                725                 730                 735

Gly Pro Ala Pro Phe Asn Leu Gln Arg Gln Gly Ser Arg Glu Asn Gly
            740                 745                 750

Ser Val Glu Ser Asp Gly Leu Thr Asn Asp Ser Ser Ser Leu Met Gly
        755                 760                 765

Asp Gln Glu Tyr Gln Ser Arg Ser Pro Asp Ile Leu Glu Thr Thr Ser
    770                 775                 780
```

```
Phe Gln Ala Leu Ser Pro Ala Asn Ser Gln Ala Glu Ser Ile Lys Ser
785                 790                 795                 800

Lys Ser Pro Asp Ala Gly Ser Lys Ala Glu Ser Ser Glu Asn Ser Arg
                805                 810                 815

Thr Glu Met Glu Gly Arg Ser Ser Leu Pro Ser Thr Phe Ile Arg Ala
            820                 825                 830

Pro Pro Thr Tyr Val Lys Val Glu Val Pro Gly Thr Phe Val Gly Pro
        835                 840                 845

Ser Thr Leu Ser Pro Gly Met Thr Pro Leu Leu Ala Ala Gln Pro Arg
    850                 855                 860

Arg Gln Ala Lys Gln His Gly Cys Thr Arg Cys Gly Lys Asn Phe Ser
865                 870                 875                 880

Ser Ala Ser Ala Leu Gln Ile His Glu Arg Thr His Thr Gly Glu Lys
                885                 890                 895

Pro Phe Val Cys Asn Ile Cys Gly Arg Ala Phe Thr Thr Lys Gly Asn
            900                 905                 910

Leu Lys Val His Tyr Met Thr His Gly Ala Asn Asn Asn Ser Ala Arg
        915                 920                 925

Arg Gly Arg Lys Leu Ala Ile Glu Asn Thr Met Ala Leu Leu Gly Thr
    930                 935                 940

Asp Gly Lys Arg Val Ser Glu Ile Phe Pro Lys Glu Ile Leu Ala Pro
945                 950                 955                 960

Ser Val Asn Val Asp Pro Val Val Trp Asn Gln Tyr Thr Ser Met Leu
                965                 970                 975

Asn Gly Gly Leu Ala Val Lys Thr Asn Glu Ile Ser Val Ile Gln Ser
            980                 985                 990

Gly Gly Val Pro Thr Leu Pro Val  Ser Leu Gly Ala Thr  Ser Val Val
        995                 1000                1005

Asn Asn  Ala Thr Val Ser Lys  Met Asp Gly Ser Gln  Ser Gly Ile
    1010                1015                1020

Ser Ala  Asp Val Glu Lys Pro  Ser Ala Thr Asp Gly  Val Pro Lys
    1025                1030                1035

His Gln  Phe Pro His Phe Leu  Glu Glu Asn Lys Ile  Ala Val Ser
    1040                1045                1050


<210> SEQ ID NO 10
<211> LENGTH: 489
<212> TYPE: PRT
<213> ORGANISM: Mus musculus

<400> SEQUENCE: 10

Met Cys Asn Thr Asn Met Ser Val Ser Thr Glu Gly Ala Ala Ser Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Asn Asp Thr Tyr
        35                  40                  45

Thr Met Lys Glu Ile Ile Phe Tyr Ile Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Val Phe Gly Val Pro Ser Phe Ser Val Lys Glu His
                85                  90                  95

Arg Lys Ile Tyr Ala Met Ile Tyr Arg Asn Leu Val Ala Val Ser Gln
```

```
            100                 105                 110

Gln Asp Ser Gly Thr Ser Leu Ser Glu Ser Arg Arg Gln Pro Glu Gly
        115                 120                 125

Gly Ser Asp Leu Lys Asp Pro Leu Gln Ala Pro Pro Glu Glu Lys Pro
    130                 135                 140

Ser Ser Ser Asp Leu Ile Ser Arg Leu Ser Thr Ser Ser Arg Arg Arg
145                 150                 155                 160

Ser Ile Ser Glu Thr Glu Glu Asn Thr Asp Glu Leu Pro Gly Glu Arg
                165                 170                 175

His Arg Lys Arg Arg Arg Ser Leu Ser Phe Asp Pro Ser Leu Gly Leu
            180                 185                 190

Cys Glu Leu Arg Glu Met Cys Ser Gly Gly Ser Ser Ser Ser Ser Ser
        195                 200                 205

Ser Ser Ser Glu Ser Thr Glu Thr Pro Ser His Gln Asp Leu Asp Asp
    210                 215                 220

Gly Val Ser Glu His Ser Gly Asp Cys Leu Asp Gln Asp Ser Val Ser
225                 230                 235                 240

Asp Gln Phe Ser Val Glu Phe Glu Val Glu Ser Leu Asp Ser Glu Asp
                245                 250                 255

Tyr Ser Leu Ser Asp Glu Gly His Glu Leu Ser Asp Glu Asp Asp Glu
            260                 265                 270

Val Tyr Arg Val Thr Val Tyr Gln Thr Gly Glu Ser Asp Thr Asp Ser
        275                 280                 285

Phe Glu Gly Asp Pro Glu Ile Ser Leu Ala Asp Tyr Trp Lys Cys Thr
    290                 295                 300

Ser Cys Asn Glu Met Asn Pro Pro Leu Pro Ser His Cys Lys Arg Cys
305                 310                 315                 320

Trp Thr Leu Arg Glu Asn Trp Leu Pro Asp Asp Lys Gly Lys Asp Lys
                325                 330                 335

Val Glu Ile Ser Glu Lys Ala Lys Leu Glu Asn Ser Ala Gln Ala Glu
            340                 345                 350

Glu Gly Leu Asp Val Pro Asp Gly Lys Lys Leu Thr Glu Asn Asp Ala
        355                 360                 365

Lys Glu Pro Cys Ala Glu Glu Asp Ser Glu Glu Lys Ala Glu Gln Thr
    370                 375                 380

Pro Leu Ser Gln Glu Ser Asp Asp Tyr Ser Gln Pro Ser Thr Ser Ser
385                 390                 395                 400

Ser Ile Val Tyr Ser Ser Gln Glu Ser Val Lys Glu Leu Lys Glu Glu
                405                 410                 415

Thr Gln Asp Lys Asp Glu Ser Val Glu Ser Ser Phe Ser Leu Asn Ala
            420                 425                 430

Ile Glu Pro Cys Val Ile Cys Gln Gly Arg Pro Lys Asn Gly Cys Ile
        435                 440                 445

Val His Gly Lys Thr Gly His Leu Met Ser Cys Phe Thr Cys Ala Lys
    450                 455                 460

Lys Leu Lys Lys Arg Asn Lys Pro Cys Pro Val Cys Arg Gln Pro Ile
465                 470                 475                 480

Gln Met Ile Val Leu Thr Tyr Phe Asn
                485
```

<210> SEQ ID NO 11
<211> LENGTH: 548
<212> TYPE: PRT
<213> ORGANISM: Homo sapiens

<400> SEQUENCE: 11

Met Asp Glu Leu Phe Pro Leu Ile Phe Pro Ala Glu Pro Ala Gln Ala
1 5 10 15

Ser Gly Pro Tyr Val Glu Ile Ile Glu Gln Pro Lys Gln Arg Gly Met
20 25 30

Arg Phe Arg Tyr Lys Cys Glu Gly Arg Ser Ala Gly Ser Ile Pro Gly
35 40 45

Glu Arg Ser Thr Asp Thr Thr Lys Thr His Pro Thr Ile Lys Ile Asn
50 55 60

Gly Tyr Thr Gly Pro Gly Thr Val Arg Ile Ser Leu Val Thr Lys Asp
65 70 75 80

Pro Pro His Arg Pro His Pro His Glu Leu Val Gly Lys Asp Cys Arg
85 90 95

Asp Gly Phe Tyr Glu Ala Glu Leu Cys Pro Asp Arg Cys Ile His Ser
100 105 110

Phe Gln Asn Leu Gly Ile Gln Cys Val Lys Lys Arg Asp Leu Glu Gln
115 120 125

Ala Ile Ser Gln Arg Ile Gln Thr Asn Asn Asn Pro Phe Gln Glu Glu
130 135 140

Gln Arg Gly Asp Tyr Asp Leu Asn Ala Val Arg Leu Cys Phe Gln Val
145 150 155 160

Thr Val Arg Asp Pro Ser Gly Arg Pro Leu Arg Leu Pro Pro Val Leu
165 170 175

Ser His Pro Ile Phe Asp Asn Arg Ala Pro Asn Thr Ala Glu Leu Lys
180 185 190

Ile Cys Arg Val Asn Arg Asn Ser Gly Ser Cys Leu Gly Gly Asp Glu
195 200 205

Ile Phe Leu Leu Cys Asp Lys Val Gln Lys Glu Asp Ile Glu Val Tyr
210 215 220

Phe Thr Gly Pro Gly Trp Glu Ala Arg Gly Ser Phe Ser Gln Ala Asp
225 230 235 240

Val His Arg Gln Val Ala Ile Val Phe Arg Thr Pro Pro Tyr Ala Asp
245 250 255

Pro Ser Leu Gln Ala Pro Val Arg Val Ser Met Gln Leu Arg Arg Pro
260 265 270

Ser Asp Arg Glu Leu Ser Glu Pro Met Glu Phe Gln Tyr Leu Pro Asp
275 280 285

Thr Asp Asp Arg His Arg Ile Glu Glu Lys Arg Lys Arg Thr Tyr Glu
290 295 300

Thr Phe Lys Ser Ile Met Lys Lys Ser Pro Phe Ser Gly Pro Thr Asp
305 310 315 320

Pro Arg Pro Pro Pro Arg Arg Ile Ala Val Pro Ser Arg Ser Ser Ala
325 330 335

Ser Val Pro Lys Pro Ala Pro Gln Pro Tyr Pro Phe Thr Ser Ser Leu
340 345 350

Ser Thr Ile Asn Tyr Asp Glu Phe Pro Thr Met Val Phe Pro Ser Gly
355 360 365

Gln Ile Ser Gln Ala Ser Ala Leu Ala Pro Ala Pro Pro Gln Val Leu
370 375 380

Pro Gln Ala Pro Ala Pro Ala Pro Ala Pro Ala Met Val Ser Ala Leu
385 390 395 400

Ala Gln Ala Pro Ala Pro Val Pro Val Leu Ala Pro Gly Pro Pro Gln

```
                405                 410                 415

Ala Val Ala Pro Pro Ala Pro Lys Pro Thr Gln Ala Gly Glu Gly Thr
            420                 425                 430

Leu Ser Glu Ala Leu Leu Gln Leu Gln Phe Asp Asp Glu Asp Leu Gly
        435                 440                 445

Ala Leu Leu Gly Asn Ser Thr Asp Pro Ala Val Phe Thr Asp Leu Ala
    450                 455                 460

Ser Val Asp Asn Ser Glu Phe Gln Gln Leu Leu Asn Gln Gly Ile Pro
465                 470                 475                 480

Val Ala Pro His Thr Thr Glu Pro Met Leu Met Glu Tyr Pro Glu Ala
                485                 490                 495

Ile Thr Arg Leu Val Thr Gly Ala Gln Arg Pro Pro Asp Pro Ala Pro
            500                 505                 510

Ala Pro Leu Gly Ala Pro Gly Leu Pro Asn Gly Leu Leu Ser Gly Asp
        515                 520                 525

Glu Asp Phe Ser Ser Ile Ala Asp Met Asp Phe Ser Ala Leu Leu Ser
    530                 535                 540

Gln Ile Ser Ser
545


<210> SEQ ID NO 12
<211> LENGTH: 319
<212> TYPE: PRT
<213> ORGANISM: Artificial Sequence
<220> FEATURE:
<223> OTHER INFORMATION: AirID_S118G

<400> SEQUENCE: 12

Met Lys Asp Asn Thr Val Pro Leu Thr Leu Ile Ser Ile Leu Ala Asp
1               5                   10                  15

Gly Glu Phe His Ser Gly Glu Gln Leu Gly Glu Gln Leu Gly Met Ser
            20                  25                  30

Arg Ala Ala Ile Asn Lys His Ile Lys Thr Leu Arg Asp Trp Gly Val
        35                  40                  45

Asp Val Phe Arg Val Gln Gly Lys Gly Tyr Cys Leu Pro Glu Pro Ile
    50                  55                  60

Gln Leu Leu Asp Glu Glu Lys Ile Arg Gln Gln Leu Asp Glu Gly Ser
65                  70                  75                  80

Val Thr Val Leu Pro Val Ile Asp Ser Thr Asn Gln Tyr Leu Leu Asp
                85                  90                  95

Arg Leu Asp Glu Leu Thr Ser Gly Asp Val Cys Ile Ala Glu Tyr Gln
            100                 105                 110

Gln Ala Gly Arg Gly Gly Arg Gly Arg Lys Trp Phe Ser Pro Phe Gly
        115                 120                 125

Ala Asn Leu Tyr Leu Ser Met Tyr Trp Arg Leu Glu Gln Gly Pro Ala
    130                 135                 140

Ala Ala Met Gly Leu Ser Leu Val Ile Gly Ile Val Met Ala Glu Thr
145                 150                 155                 160

Leu Gln Lys Leu Gly Ala Asp Gly Val Arg Val Lys Trp Pro Asn Asp
                165                 170                 175

Leu Tyr Leu Asn Asp Arg Lys Leu Ala Gly Ile Leu Val Glu Met Thr
            180                 185                 190

Gly Lys Thr Gly Asp Ala Ala His Ile Val Ile Gly Ala Gly Ile Asn
        195                 200                 205

Leu Ser Met Arg Glu Pro Glu Thr Asp Glu Val Asp Gln Ser Trp Ile
```

```
    210                 215                 220

Asn Leu Gln Glu Ala Gly Ile Thr Ile Asp Arg Asn Gln Leu Ala Ala
225                 230                 235                 240

Arg Leu Ile Lys Asp Leu Arg Ser Ala Leu Arg Gln Phe Glu Gln Gln
                245                 250                 255

Gly Leu Ala Pro Phe Leu Ser Arg Trp Glu Ala Leu Asp Asn Phe Ile
            260                 265                 270

Asn Arg Pro Val Lys Leu Ile Ile Gly Asp Arg Glu Ile His Gly Ile
        275                 280                 285

Ala Arg Gly Ile Asn Glu Gln Gly Ala Leu Leu Leu Glu Gln Asp Gly
    290                 295                 300

Val Ile Lys Pro Trp Ile Gly Gly Glu Ile Ser Leu Arg Ser Ala
305                 310                 315


<210> SEQ ID NO 13
<211> LENGTH: 319
<212> TYPE: PRT
<213> ORGANISM: Artificial Sequence
<220> FEATURE:
<223> OTHER INFORMATION: AVVA-R118S

<400> SEQUENCE: 13

Met Ser Glu Gln Trp Ser Arg Lys Arg Glu Ile Leu Ala Leu Leu Ser
1               5                   10                  15

Ser Gly His Phe Val Ser Gly Glu Glu Leu Ala Thr Gln Leu Gly Ile
            20                  25                  30

Ser Arg Thr Ala Val Ser Lys His Ile Ala Ala Leu Glu Glu Tyr Gly
        35                  40                  45

Val Asp Ile Tyr Ser Val Lys Gly Lys Gly Tyr Lys Leu Ala Asn Pro
    50                  55                  60

Ile Ser Leu Ile Asp Glu Ser Lys Leu Lys Ser Ala Ile Asn Asn Arg
65                  70                  75                  80

Cys Phe Tyr Phe Asp Glu Ile Pro Ser Thr Asn Gly Phe Met Leu Lys
                85                  90                  95

His Ala Glu Glu Leu Lys Ser Gly Asp Ile Cys Val Ala Glu Tyr Gln
            100                 105                 110

Ser Ala Gly Arg Gly Ser Arg Gly Arg Thr Trp Val Ser Pro Tyr Gly
        115                 120                 125

Cys His Leu Tyr Phe Ser Leu Tyr Trp Arg Phe Pro Gln Gly Met Ala
    130                 135                 140

Gln Ala Met Gly Leu Ser Leu Val Val Ala Cys Ser Leu Val Lys Val
145                 150                 155                 160

Leu Lys Ser Phe Gly Val Asp Gly Val Gly Val Lys Trp Pro Asn Asp
                165                 170                 175

Ile Tyr Leu Asn His Lys Lys Leu Ala Gly Val Leu Ile Glu Met Ser
            180                 185                 190

Gly Gln Ala Asp Ser Glu Cys His Leu Val Ile Gly Ile Gly Ile Asn
        195                 200                 205

Met Ala Met Ser Glu Gln Gln Gly Lys Lys Ile Asp Gln Pro Trp Ser
    210                 215                 220

Asp Leu Ser Ser Leu Thr Ser Met Pro Asp Lys Thr Glu Leu Leu Ile
225                 230                 235                 240

Ala Leu Gln Lys Gln Leu Lys Gln Asp Leu Glu Leu Phe Glu Arg Glu
                245                 250                 255

Gly Leu Lys Ala Phe Gln Pro Arg Trp Gln Glu Ala Asp Leu Phe Tyr
```

```
            260                 265                 270

Gly Lys Gln Ile Lys Leu Leu Met Gly Glu Asn Gln Val Glu Gly Ile
        275                 280                 285

Cys Arg Gly Ile Asp Glu Gln Gly Ala Val Leu Leu Glu Thr Asp Asp
    290                 295                 300

Gly Ile Gln Ala Phe Ile Gly Gly Glu Ile Ser Leu Arg Ala Ala
305                 310                 315


<210> SEQ ID NO 14
<211> LENGTH: 319
<212> TYPE: PRT
<213> ORGANISM: Artificial Sequence
<220> FEATURE:
<223> OTHER INFORMATION: AVVA-R118G

<400> SEQUENCE: 14

Met Ser Glu Gln Trp Ser Arg Lys Arg Glu Ile Leu Ala Leu Leu Ser
1               5                   10                  15

Ser Gly His Phe Val Ser Gly Glu Glu Leu Ala Thr Gln Leu Gly Ile
            20                  25                  30

Ser Arg Thr Ala Val Ser Lys His Ile Ala Ala Leu Glu Glu Tyr Gly
        35                  40                  45

Val Asp Ile Tyr Ser Val Lys Gly Lys Gly Tyr Lys Leu Ala Asn Pro
    50                  55                  60

Ile Ser Leu Ile Asp Glu Ser Lys Leu Lys Ser Ala Ile Asn Asn Arg
65                  70                  75                  80

Cys Phe Tyr Phe Asp Glu Ile Pro Ser Thr Asn Gly Phe Met Leu Lys
                85                  90                  95

His Ala Glu Glu Leu Lys Ser Gly Asp Ile Cys Val Ala Glu Tyr Gln
            100                 105                 110

Ser Ala Gly Arg Gly Gly Arg Gly Arg Thr Trp Val Ser Pro Tyr Gly
        115                 120                 125

Cys His Leu Tyr Phe Ser Leu Tyr Trp Arg Phe Pro Gln Gly Met Ala
    130                 135                 140

Gln Ala Met Gly Leu Ser Leu Val Val Ala Cys Ser Leu Val Lys Val
145                 150                 155                 160

Leu Lys Ser Phe Gly Val Asp Gly Val Gly Val Lys Trp Pro Asn Asp
                165                 170                 175

Ile Tyr Leu Asn His Lys Lys Leu Ala Gly Val Leu Ile Glu Met Ser
            180                 185                 190

Gly Gln Ala Asp Ser Glu Cys His Leu Val Ile Gly Ile Gly Ile Asn
        195                 200                 205

Met Ala Met Ser Glu Gln Gln Gly Lys Lys Ile Asp Gln Pro Trp Ser
    210                 215                 220

Asp Leu Ser Ser Leu Thr Ser Met Pro Asp Lys Thr Glu Leu Leu Ile
225                 230                 235                 240

Ala Leu Gln Lys Gln Leu Lys Gln Asp Leu Glu Leu Phe Glu Arg Glu
                245                 250                 255

Gly Leu Lys Ala Phe Gln Pro Arg Trp Gln Glu Ala Asp Leu Phe Tyr
            260                 265                 270

Gly Lys Gln Ile Lys Leu Leu Met Gly Glu Asn Gln Val Glu Gly Ile
        275                 280                 285

Cys Arg Gly Ile Asp Glu Gln Gly Ala Val Leu Leu Glu Thr Asp Asp
    290                 295                 300

Gly Ile Gln Ala Phe Ile Gly Gly Glu Ile Ser Leu Arg Ala Ala
```

305 310 315

<210> SEQ ID NO 15
<211> LENGTH: 319
<212> TYPE: PRT
<213> ORGANISM: Artificial Sequence
<220> FEATURE:
<223> OTHER INFORMATION: AVVA-R118S,Q141R

<400> SEQUENCE: 15

Met Ser Glu Gln Trp Ser Arg Lys Arg Glu Ile Leu Ala Leu Leu Ser
1 5 10 15

Ser Gly His Phe Val Ser Gly Glu Glu Leu Ala Thr Gln Leu Gly Ile
20 25 30

Ser Arg Thr Ala Val Ser Lys His Ile Ala Ala Leu Glu Glu Tyr Gly
35 40 45

Val Asp Ile Tyr Ser Val Lys Gly Lys Gly Tyr Lys Leu Ala Asn Pro
50 55 60

Ile Ser Leu Ile Asp Glu Ser Lys Leu Lys Ser Ala Ile Asn Asn Arg
65 70 75 80

Cys Phe Tyr Phe Asp Glu Ile Pro Ser Thr Asn Gly Phe Met Leu Lys
85 90 95

His Ala Glu Glu Leu Lys Ser Gly Asp Ile Cys Val Ala Glu Tyr Gln
100 105 110

Ser Ala Gly Arg Gly Ser Arg Gly Arg Thr Trp Val Ser Pro Tyr Gly
115 120 125

Cys His Leu Tyr Phe Ser Leu Tyr Trp Arg Phe Pro Arg Gly Met Ala
130 135 140

Gln Ala Met Gly Leu Ser Leu Val Val Ala Cys Ser Leu Val Lys Val
145 150 155 160

Leu Lys Ser Phe Gly Val Asp Gly Val Gly Val Lys Trp Pro Asn Asp
165 170 175

Ile Tyr Leu Asn His Lys Lys Leu Ala Gly Val Leu Ile Glu Met Ser
180 185 190

Gly Gln Ala Asp Ser Glu Cys His Leu Val Ile Gly Ile Gly Ile Asn
195 200 205

Met Ala Met Ser Glu Gln Gln Gly Lys Lys Ile Asp Gln Pro Trp Ser
210 215 220

Asp Leu Ser Ser Leu Thr Ser Met Pro Asp Lys Thr Glu Leu Leu Ile
225 230 235 240

Ala Leu Gln Lys Gln Leu Lys Gln Asp Leu Glu Leu Phe Glu Arg Glu
245 250 255

Gly Leu Lys Ala Phe Gln Pro Arg Trp Gln Glu Ala Asp Leu Phe Tyr
260 265 270

Gly Lys Gln Ile Lys Leu Leu Met Gly Glu Asn Gln Val Glu Gly Ile
275 280 285

Cys Arg Gly Ile Asp Glu Gln Gly Ala Val Leu Leu Glu Thr Asp Asp
290 295 300

Gly Ile Gln Ala Phe Ile Gly Gly Glu Ile Ser Leu Arg Ala Ala
305 310 315

<210> SEQ ID NO 16
<211> LENGTH: 319
<212> TYPE: PRT
<213> ORGANISM: Artificial Sequence
<220> FEATURE:
<223> OTHER INFORMATION: AVVA-R118G,Q141R

<400> SEQUENCE: 16

```
Met Ser Glu Gln Trp Ser Arg Lys Arg Glu Ile Leu Ala Leu Leu Ser
1               5                   10                  15

Ser Gly His Phe Val Ser Gly Glu Glu Leu Ala Thr Gln Leu Gly Ile
            20                  25                  30

Ser Arg Thr Ala Val Ser Lys His Ile Ala Ala Leu Glu Glu Tyr Gly
        35                  40                  45

Val Asp Ile Tyr Ser Val Lys Gly Lys Gly Tyr Lys Leu Ala Asn Pro
    50                  55                  60

Ile Ser Leu Ile Asp Glu Ser Lys Leu Lys Ser Ala Ile Asn Asn Arg
65                  70                  75                  80

Cys Phe Tyr Phe Asp Glu Ile Pro Ser Thr Asn Gly Phe Met Leu Lys
                85                  90                  95

His Ala Glu Glu Leu Lys Ser Gly Asp Ile Cys Val Ala Glu Tyr Gln
            100                 105                 110

Ser Ala Gly Arg Gly Gly Arg Gly Arg Thr Trp Val Ser Pro Tyr Gly
        115                 120                 125

Cys His Leu Tyr Phe Ser Leu Tyr Trp Arg Phe Pro Arg Gly Met Ala
    130                 135                 140

Gln Ala Met Gly Leu Ser Leu Val Val Ala Cys Ser Leu Val Lys Val
145                 150                 155                 160

Leu Lys Ser Phe Gly Val Asp Gly Val Gly Val Lys Trp Pro Asn Asp
                165                 170                 175

Ile Tyr Leu Asn His Lys Lys Leu Ala Gly Val Leu Ile Glu Met Ser
            180                 185                 190

Gly Gln Ala Asp Ser Glu Cys His Leu Val Ile Gly Ile Gly Ile Asn
        195                 200                 205

Met Ala Met Ser Glu Gln Gln Gly Lys Lys Ile Asp Gln Pro Trp Ser
    210                 215                 220

Asp Leu Ser Ser Leu Thr Ser Met Pro Asp Lys Thr Glu Leu Leu Ile
225                 230                 235                 240

Ala Leu Gln Lys Gln Leu Lys Gln Asp Leu Glu Leu Phe Glu Arg Glu
                245                 250                 255

Gly Leu Lys Ala Phe Gln Pro Arg Trp Gln Glu Ala Asp Leu Phe Tyr
            260                 265                 270

Gly Lys Gln Ile Lys Leu Leu Met Gly Glu Asn Gln Val Glu Gly Ile
        275                 280                 285

Cys Arg Gly Ile Asp Glu Gln Gly Ala Val Leu Leu Glu Thr Asp Asp
    290                 295                 300

Gly Ile Gln Ala Phe Ile Gly Gly Glu Ile Ser Leu Arg Ala Ala
305                 310                 315
```